United States Patent
White et al.

(10) Patent No.: US 10,861,590 B2
(45) Date of Patent: Dec. 8, 2020

(54) GENERATING SPATIAL VISUALIZATIONS OF A PATIENT MEDICAL STATE

(71) Applicant: Optum, Inc., Minnetonka, MN (US)

(72) Inventors: Patrick White, Basking Ridge, NJ (US); Anthony Degliomini, Basking Ridge, NJ (US); Somadev Pasala, Montclair, NJ (US)

(73) Assignee: Optum, Inc., Minnetonka, MN (US)

( * ) Notice: Subject to any disclaimer, the term of this patent is extended or adjusted under 35 U.S.C. 154(b) by 0 days.

(21) Appl. No.: 16/246,789

(22) Filed: Jan. 14, 2019

(65) Prior Publication Data
US 2020/0027532 A1  Jan. 23, 2020

Related U.S. Application Data

(63) Continuation of application No. 62/700,602, filed on Jul. 19, 2018.

(51) Int. Cl.
*G06T 15/00* (2011.01)
*G16H 10/60* (2018.01)
(Continued)

(52) U.S. Cl.
CPC .......... *G16H 10/60* (2018.01); *G06F 40/295* (2020.01); *G06N 20/10* (2019.01); *G06T 19/00* (2013.01);
(Continued)

(58) Field of Classification Search
CPC .............. G06T 2219/004; G06T 19/00; G06T 2200/24; G06F 40/295; G06N 20/10; G16H 50/30; G16H 10/60; G16H 50/20
(Continued)

(56) References Cited

U.S. PATENT DOCUMENTS 6,266,645 B1   7/2001   Simpson
6,556,977 B1   4/2003   Lapointe et al.
(Continued)

FOREIGN PATENT DOCUMENTS

WO   2014/201515 A1   12/2014

OTHER PUBLICATIONS

Bui AA, Hsu W. Medical data visualization: Toward integrated clinical workstations. InMedical Imaging Informatics 2010 (pp. 139-193). Springer, Boston, MA.*
(Continued)

*Primary Examiner* — Phu K Nguyen
(74) *Attorney, Agent, or Firm* — Alston & Bird LLP

(57) ABSTRACT

A three-dimensional visualization of patient medical information is provided via a user interface of a user computing entity. Responsive to receiving user input, the user computing entity transmits a visualization request that comprises a patient indication and a desired visualization type indication. The user computing entity receives a three-dimensional visualization corresponding to the patient indication and the desired visualization type indication. The three-dimensional visualization is generated by mapping one or more medical codes each to a corresponding set of x, y, z coordinates. The three-dimensional visualization is displayed via the interactive user interface and comprises (a) a graphical representation of a human body corresponding to the x, y, z coordinates and (b) one or more points and/or zones. Each point and/or zone (i) is mapped to a location on the graphical representation of the human body via a body coordinate and (ii) corresponds to a medical code.

16 Claims, 10 Drawing Sheets

(51) Int. Cl.
  *G16H 50/20*   (2018.01)
  *G06N 20/10*   (2019.01)
  *G06F 40/295*  (2020.01)
  *G06T 19/00*   (2011.01)

(52) U.S. Cl.
  CPC ......... *G16H 50/20* (2018.01); *G06T 2200/24* (2013.01); *G06T 2219/004* (2013.01)

(58) Field of Classification Search
  USPC .......................................................... 345/418
  See application file for complete search history.

(56) References Cited

U.S. PATENT DOCUMENTS

| | | | |
|---|---|---|---|
| 6,915,254 | B1 | 7/2005 | Heinze et al. |
| 7,499,048 | B2 * | 3/2009 | Sieracki ................... A61B 5/00 345/156 |
| 7,801,839 | B2 | 9/2010 | Kates et al. |
| 8,255,412 | B2 | 8/2012 | Gao et al. |
| 8,296,247 | B2 | 10/2012 | Zhang et al. |
| 8,320,651 | B2 * | 11/2012 | Vining ................... G06F 19/321 382/128 |
| 8,504,392 | B2 | 8/2013 | Saria et al. |
| 8,856,156 | B1 | 10/2014 | McNair et al. |
| 8,963,914 | B2 * | 2/2015 | Rawat ..................... G06T 17/00 345/419 |
| 9,805,160 | B2 | 10/2017 | Morris et al. |
| 9,828,671 | B2 * | 11/2017 | Shibusawa .............. C23C 16/26 |
| 10,176,645 | B2 * | 1/2019 | Canfield ................. G06T 19/20 |
| 2005/0240439 | A1 | 10/2005 | Covit et al. |
| 2008/0288292 | A1 | 11/2008 | Bi et al. |
| 2012/0033871 | A1 * | 2/2012 | Vining ................... G06F 19/321 382/132 |
| 2012/0166212 | A1 | 6/2012 | Campbell |
| 2012/0185275 | A1 | 7/2012 | Loghmani |
| 2013/0080187 | A1 | 3/2013 | Bacon et al. |
| 2014/0249849 | A1 | 9/2014 | Khare et al. |
| 2014/0278490 | A1 | 9/2014 | Namazifar et al. |
| 2015/0095016 | A1 | 4/2015 | Karres et al. |
| 2015/0356198 | A1 | 12/2015 | D'Souza et al. |
| 2016/0012202 | A1 | 1/2016 | Hu et al. |
| 2016/0063214 | A1 | 3/2016 | Blue |
| 2016/0092641 | A1 | 3/2016 | Delaney et al. |
| 2017/0132288 | A1 | 5/2017 | Ho et al. |
| 2017/0161619 | A1 | 6/2017 | Franceschini et al. |
| 2017/0308981 | A1 | 10/2017 | Razavian et al. |
| 2018/0025121 | A1 | 1/2018 | Fei et al. |
| 2018/0089382 | A1 | 3/2018 | Allen et al. |
| 2018/0089383 | A1 | 3/2018 | Allen et al. |
| 2018/0165418 | A1 | 6/2018 | Swartz et al. |
| 2018/0260381 | A1 | 9/2018 | Carreras et al. |
| 2018/0293499 | A1 | 10/2018 | He et al. |
| 2018/0315440 | A1 | 11/2018 | Inaba et al. |
| 2019/0005019 | A1 | 1/2019 | Burke et al. |
| 2019/0096140 | A1 * | 3/2019 | Canfield ................. A61B 8/488 |
| 2019/0114318 | A1 | 4/2019 | Zhou et al. |
| 2019/0171792 | A1 | 6/2019 | Manica et al. |
| 2019/0188271 | A1 | 6/2019 | Murdock et al. |
| 2019/0188848 | A1 | 6/2019 | Madani et al. |
| 2019/0220694 | A1 | 7/2019 | Biswas et al. |
| 2019/0236206 | A1 | 8/2019 | Chowdhury et al. |
| 2019/0251084 | A1 | 8/2019 | Wang et al. |
| 2019/0286759 | A1 | 9/2019 | Wilkins et al. |
| 2020/0034366 | A1 | 1/2020 | Kivatinos et al. |
| 2020/0251219 | A1 | 8/2020 | Fukunishi |

OTHER PUBLICATIONS

Shi L, Sun J, Yang Y, Ling T, Wang M, Gu Y, Yang Z, Hua Y, Zhang J. Three-dimensional visual patient based on electronic medical diagnostic records. IEEE journal of biomedical and health informatics. May 7, 2017;22(1):161-72.*

General Surgery; Basicmedical Key, Diseases of the Respiratory System: (ICD-10-CM Chapter 10, Codes J00-J99), Jun. 3, 2017.*

Feng, Yujuan et al. "Patient Outcome Prediction Via Convolutional Neural Networks Based on Multi-Granularity Medical Concept Embedding," 2017 IEEE International Converence on Bioinformatics and Biomedicine (BIBM), Nov. 13, 2017, pp. 770-777.

International Searching Authority, International Search Report and Written Opinion for International Application No. PCT/US2019/041784, dated Nov. 27, 2019, (18 pages), European Patent Office, Rijswijk, The Netherlands.

U.S. Patent and Trademark Office, NonFinal Office Action for U.S. Appl. No. 15/927,188, dated May 26, 2020, (35 pages), USA.

Wang et al., "Diagnosis Code Assignment Using Sparsity-Based Disease Correlation Embedding," Journal of Latex Class Files, vol. 13, No. 9, Sep. 2014, pp. 1-13.

Shubham Agarwal, Word to Vectors—Natural Language Processing, May 18, 2017, https://towardsdatascience.com/word-to-vectors-natural-language-processing-b253dd0b0817, Apr. 17, 2019.

Pakhomov, S., et al., Automating the Assignment of Diagnosis Codes to Patient Encounters using Example-based and Machine Learning Techniques, Sep. 1, 2006, Journal of the American Medical Informatics Association, 516-525, 13(5).

Okamoto, K., et al., Automatic DPC code selection from discharge summaries using several machine learning methods, Dec. 1, 2011, Transactions of Japanese Society for Medical and Biological Engineering, 40-47, 49/1, https://www.jstage.jst.go.jp/article/jsmbe/49/1/49_1_40/_pdf/-char/ja, Aug. 14, 2018 (Japanese Article—English Abstract only).

Lingren, T., et al., Electronic Health Record Based Algorithm to Identify Patients with Autism Spectrum Disorder, Jul. 29, 2016, PLOS One, 1-16, http://nrs.harvard.edu/um-3:HUL.InstRepos:29002605, Aug. 14, 2018.

Jara, J. L., et al., Empirical evaluation of three machine learning method for automatic classification of neoplastic diagnoses/ Evaluación empírica de tres métodos de aprendizaje automático para clasificar automáticamente diagnósticos de neoplasias, Dec. 1, 2011, Ingeniare. Revista chilena de ingenieria, 359-368, 19/3, https://scielo.conicyt.cl/pdf/ingeniare/v19n3/art06.pdf, Aug. 14, 2018.

Gonzenbach, "Sentiment Classification and Medical Health Record Analysis Using Convolutional Neural Networks," Swiss Federal Institute of Technology Zurich, May 24, 2016, pp. 1-56.

United States Patent and Trademark Office, Notice of Allowance for U.S. Appl. No. 15/927,188, dated Sep. 22, 2020, (10 pages), U.S.

* cited by examiner

| Medical Code | Body Part | Body Coordinate |
|---|---|---|
| S00.11 | right eyelid | 20, 80, 5 |
| ... | ... | ... |
| M79.672 | left foot | -30, -80, -8 |

600

GENERATING SPATIAL VISUALIZATIONS OF A PATIENT MEDICAL STATE

CROSS-REFERENCE TO RELATED APPLICATIONS

This application claims priority to U.S. Application No. 62/700,602, filed Jul. 19, 2018, the content of which is incorporated herein by reference in its entirety.

FIELD

Various embodiments relate generally to generating and/or providing a visualization of medical information corresponding to a patient. An example embodiment provides and/or generates a visualization providing a graphical representation of a past, current, or predicted future medical state of a patient.

BACKGROUND

Medical information is often encoded using medical codes, such as diagnoses codes, procedure codes, prescription or drug codes, equipment codes, revenue codes, place of service codes, and/or the like. These medical codes are non-interpretable, alpha-numeric strings that can be quite specific. For example, a fracture of the left forearm may have a specific code that is different from the code for a fracture of the right forearm. Thus, trying to identify cohorts of similar patients or patients having similar health histories may be quite difficult. For example, a key word search may identify groups of patients that have one element of their medical histories in common, but that have generally different health histories and/or conditions. For example, two patients may both have type 2 diabetes, but are vastly different in their underlying health conditions. Additionally, type 2 diabetes is highly correlated to hypertension, but people with hypertension would be considered as an unrelated population according to the key word search strategy.

BRIEF SUMMARY

Various embodiments provide methods, apparatuses, computer program products, systems, and/or the like for providing a user interface for providing a visualization of a past, current, and/or predicted future medical state of a patient. For example, in various embodiments, a set of medical codes are each mapped to a point or zone of the human body identified via at least one set of body coordinates. Various embodiments provide methods, apparatuses, computer program products, systems, and/or the like that use the visualization of the patient's past, current, or predicted future medical state and/or body coordinates corresponding to one or more medical codes to determine a predicted future medical state of the patient, identify a cohort of patients that are similar to the patient, determine a suggested medical code corresponding to a current medical state of the patient, and/or the like. In various embodiments, the visualization comprises a graphical representation of a human body and one or more points and/or zones that are mapped to locations on the graphical representation of the human body. Each point and/or zone corresponds to a medical code and the location to which the point and/or zone is mapped on the graphical representation of the human body corresponds to a body part associated with the corresponding medical code. The visualization may be used to provide a visual representation of a patient's medical history (e.g., a past or current medical state of the patient) or to provide a visual representation of a predicted future medical state of the patient. In an example embodiment, a current medical state may include a suggested medical code (and/or a corresponding point and/or zone mapped to a position on a graphical representation of the patient) that is a determined based on the patient's medical history and/or current symptoms.

Various embodiments provide a spatially-based medical state model. For example, the spatially-based medical state model may be configured to predict a future medical state of a patient based on the body coordinates that represent a past or present medical state of the patient. The past or present medical state corresponds to medical codes of the patient's medical history. In another example, the spatially-based medical state model may be configured to suggest one or more medical codes corresponding to a current medical state of the patient based on the body coordinates that represent a past or present medical state of the patient and/or body coordinates corresponding the patient's current symptoms.

According to one aspect of the present invention a method for providing a three-dimensional visualization of patient medical information is provided. In an example embodiment, the three-dimensional visualization is provided via a user interface of a user computing entity is provided. In an example embodiment, the user computing entity comprises at least one processor, at least one memory storing computer program code, and a communication interface configured to communicate via at least one network. In an example embodiment, the at least one processor of the user computing entity is in communication with a display device and at least one input device. The method comprises responsive to receiving user input, transmitting, by a user computing entity, a visualization request. The visualization request comprises (i) a patient indication and (ii) a visualization type indication. At least one of (i) the patient indication or (ii) the visualization type indication is determined based on the user input. The method further comprises receiving, by the user computing entity, a three-dimensional visualization corresponding to (a) the patient indication and (b) the visualization type indication. The three-dimensional visualization is generated by mapping one or more medical codes each to a corresponding set of x, y, z coordinates. The method further comprises causing, by the user computing entity, the three-dimensional visualization to be displayed via an interactive user interface. The three-dimensional visualization comprises (a) a graphical representation of a human body corresponding to the x, y, z coordinates and (b) one or more points and/or zones. Each point and/or zone (i) is mapped to a location on the graphical representation of the human body via a set of body coordinates and (ii) corresponds to a medical code.

According to another aspect of the present invention, an apparatus is provided. The apparatus comprises at least one processor and at least one memory including computer program code for one or more programs. The at least one processor is in communication with a display device and at least one input device. The at least one memory and the computer program code are configured to, with the at least one processor, cause the apparatus to perform at least the following, responsive to receiving user input, transmit a visualization request. The visualization request comprises (i) a patient indication and (ii) a visualization type indication. At least one of (i) the patient indication or (ii) the visualization type indication is determined based on the user input. The at least one memory and the computer program code are further configured to, with the at least one processor, cause the apparatus to perform at least receive a three-dimensional visualization corresponding to (a) the patient indication and (b) the visualization type indication. The three-dimensional visualization is generated by mapping one or more medical codes each to a corresponding set of x, y, z coordinates. The at least one memory and the computer program code are further configured to, with the at least one processor, cause the apparatus to perform at least cause the three-dimensional visualization to be displayed via an interactive user interface. The three-dimensional visualization comprises (a) a graphical representation of a human body corresponding to the x, y, z coordinates and (b) one or more points and/or zones. Each point and/or zone (i) is mapped to a location on the graphical representation of the human body via a set of body coordinates and (ii) corresponds to a medical code.

According to yet another aspect of the present invention, a computer program product is provided. The computer program product comprises at least one non-transitory computer-readable storage medium having computer-executable program code portions stored therein. The computer-executable program code portions comprise program code instructions. The computer program code instructions, when executed by a processor of a computing entity, are configured to cause the computing entity to at least, responsive to receiving user input, transmit a visualization request. The visualization request comprises (i) a patient indication and (ii) a visualization type indication. At least one of (i) the patient indication or (ii) the visualization type indication is determined based on the user input. The computer program code instructions, when executed by a processor of a computing entity, are further configured to cause the computing entity to at least receive a three-dimensional visualization corresponding to (a) the patient indication and (b) the visualization type indication. The three-dimensional visualization is generated by mapping one or more medical codes each to a corresponding set of x, y, z coordinates. The computer program code instructions, when executed by a processor of a computing entity, are further configured to cause the computing entity to at least cause the three-dimensional visualization to be displayed via an interactive user interface. The three-dimensional visualization comprises (a) a graphical representation of a human body corresponding to the x, y, z coordinates and (b) one or more points and/or zones. Each point and/or zone (i) is mapped to a location on the graphical representation of the human body via a set of body coordinates and (ii) corresponds to a medical code.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 4:
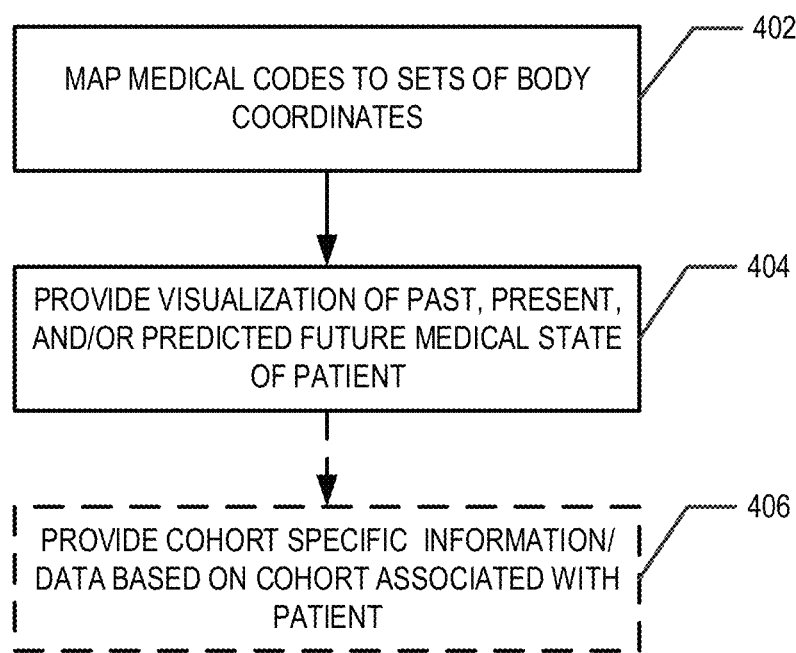
Figure 5:
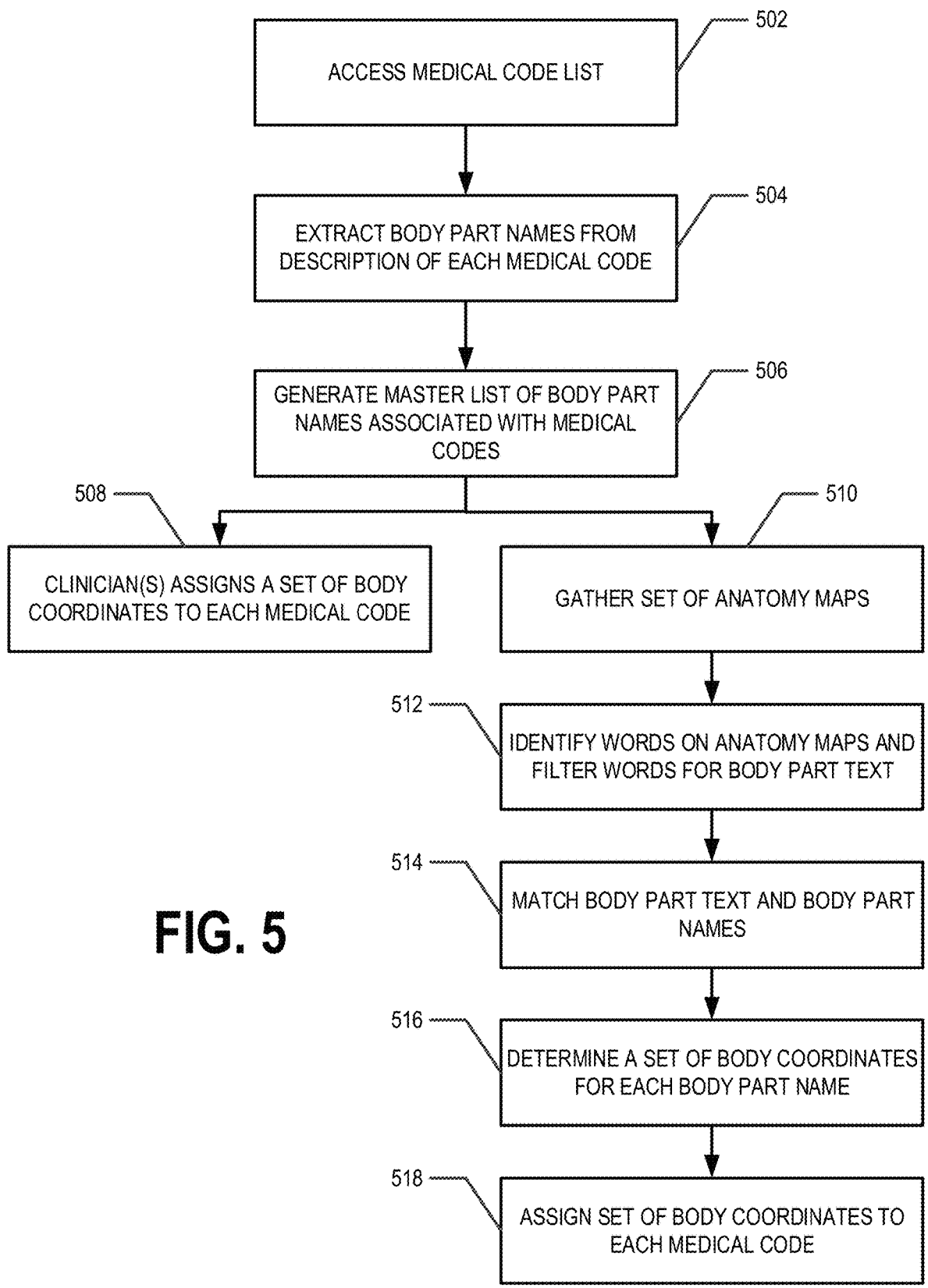
Figures 6, 7:
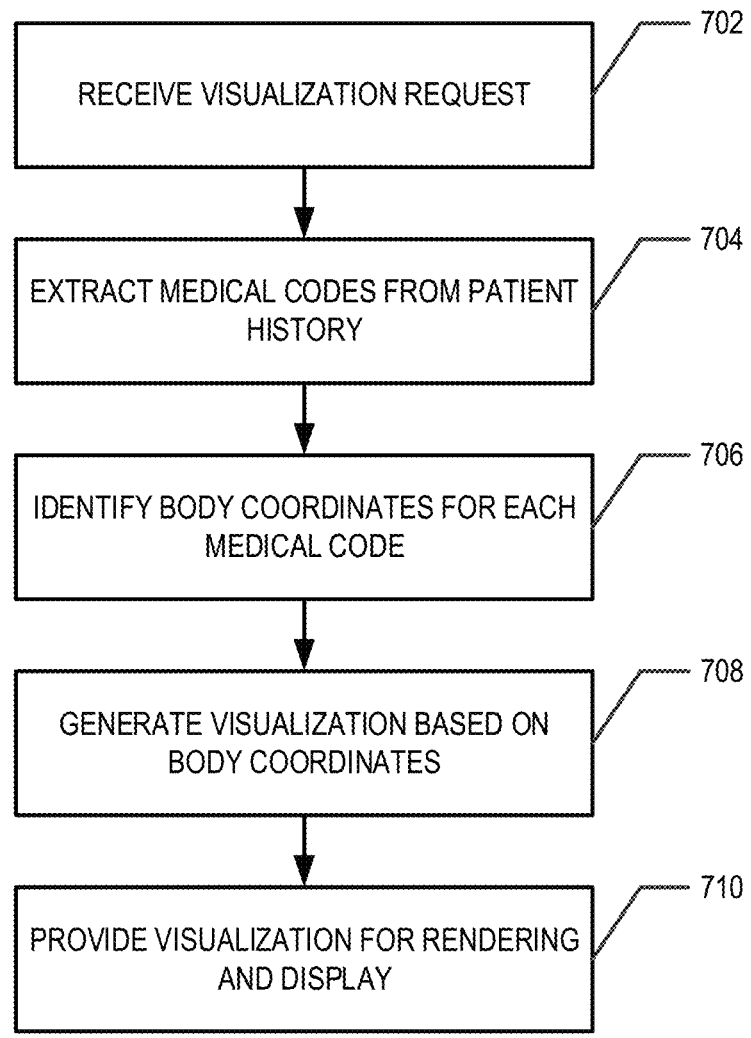
Figure 8:
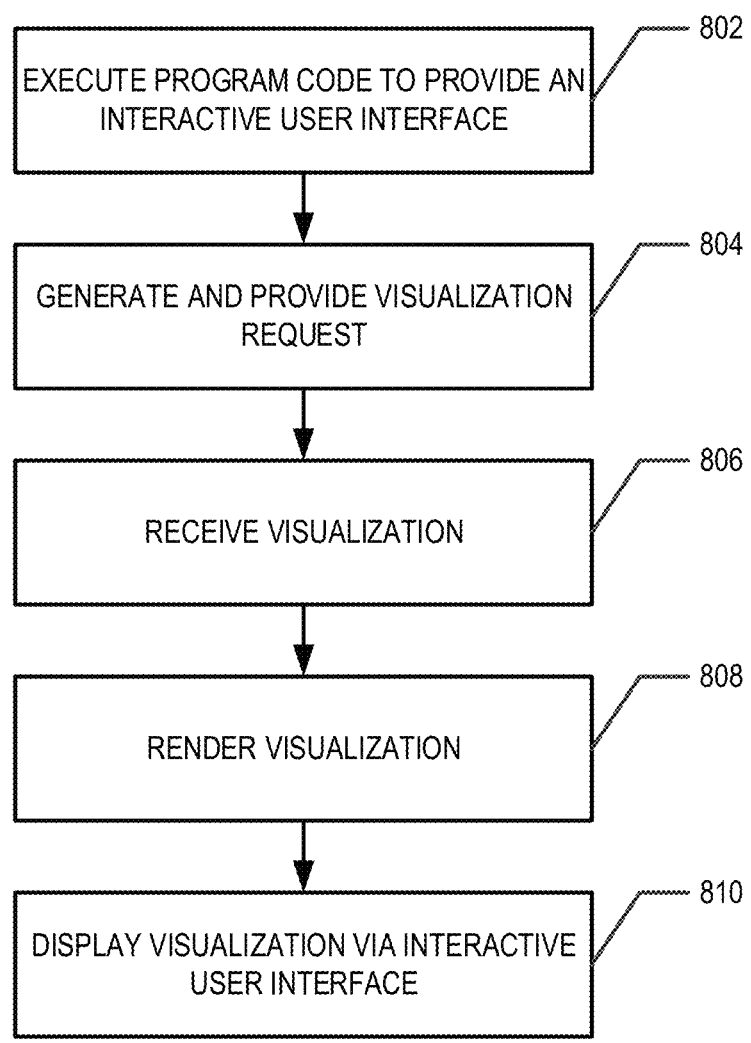
Figure 9A:
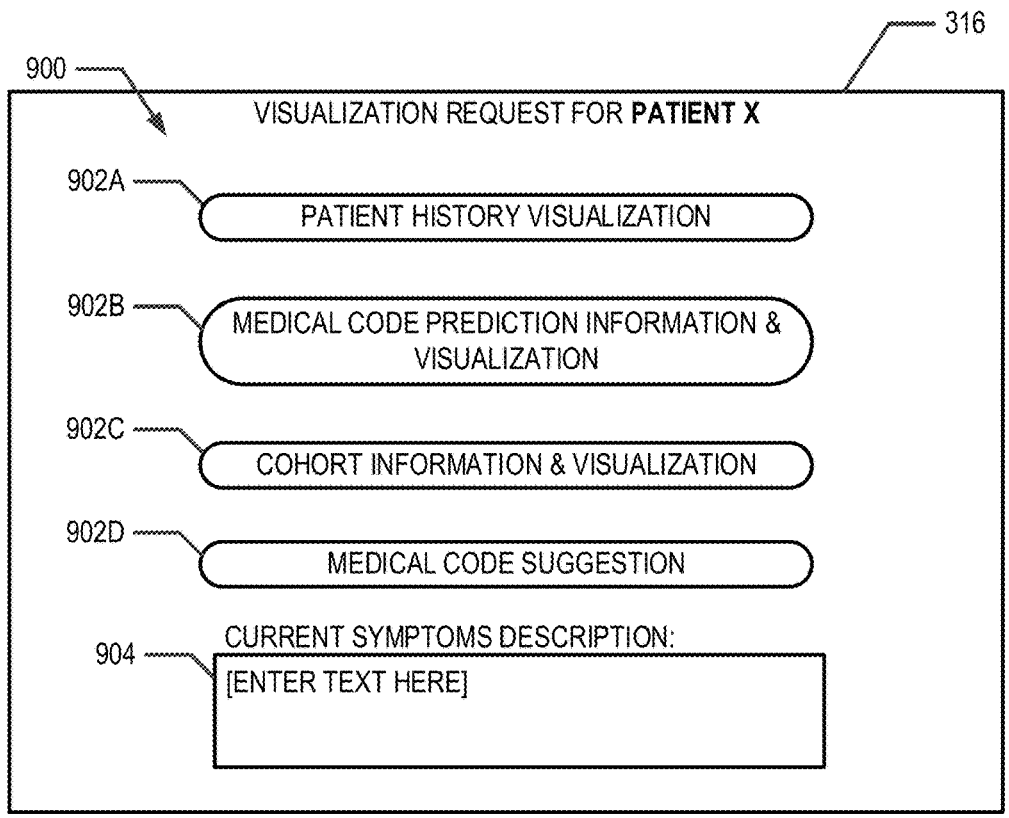
Figure 9B:
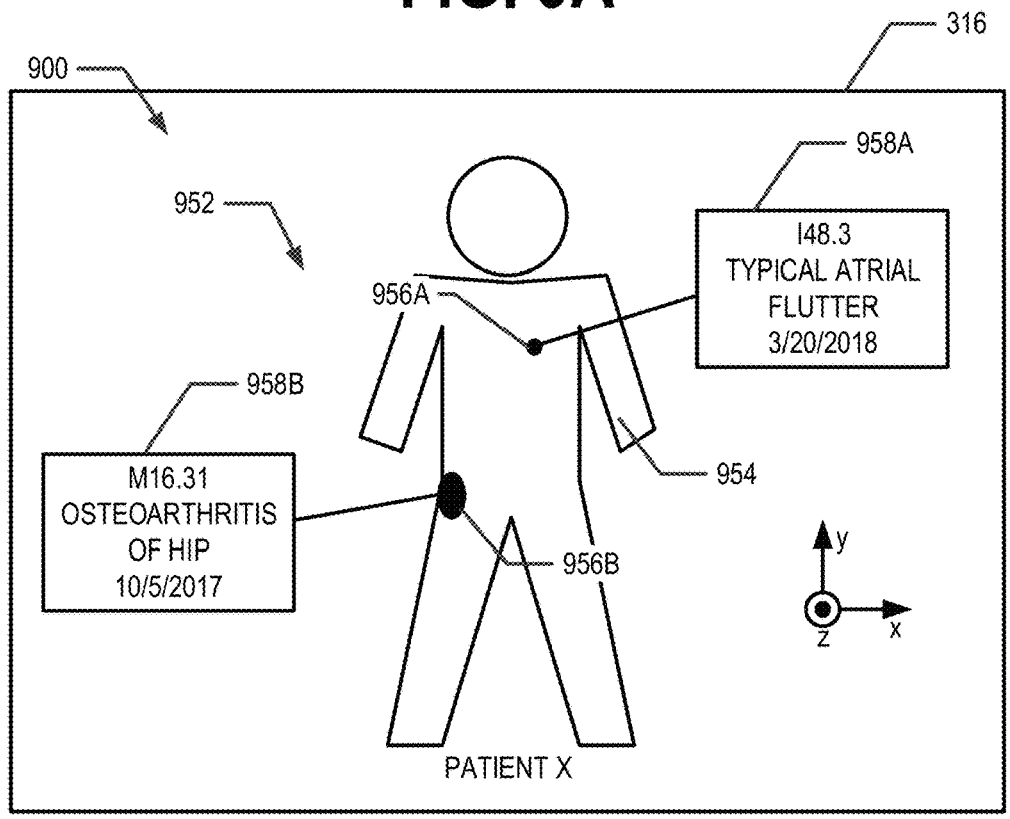
Figure 10:
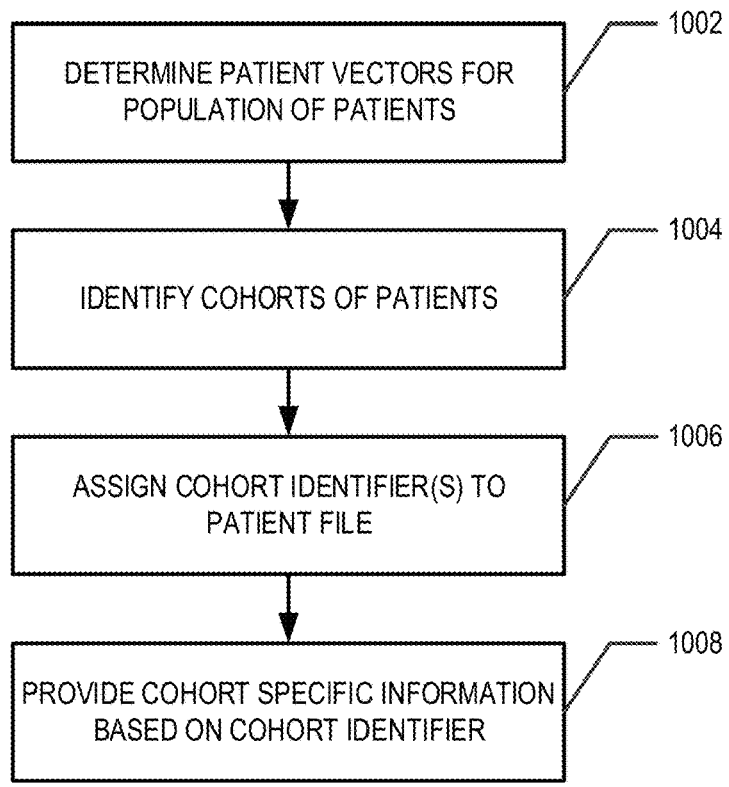
Figure 11:
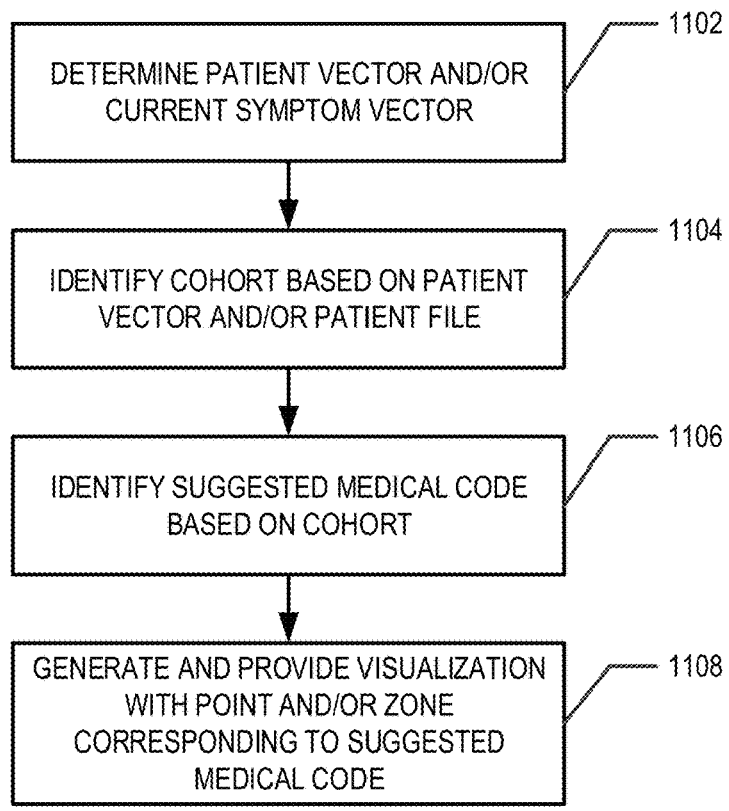
Figure 12:
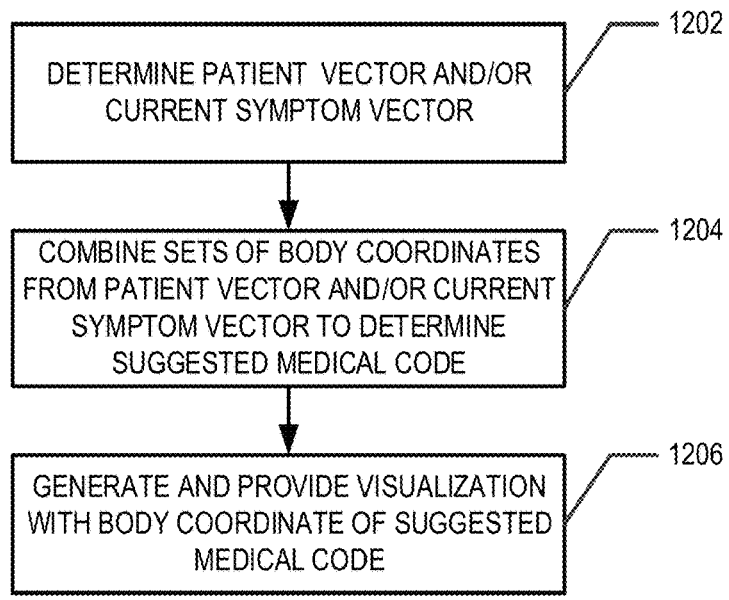
Figure 13:
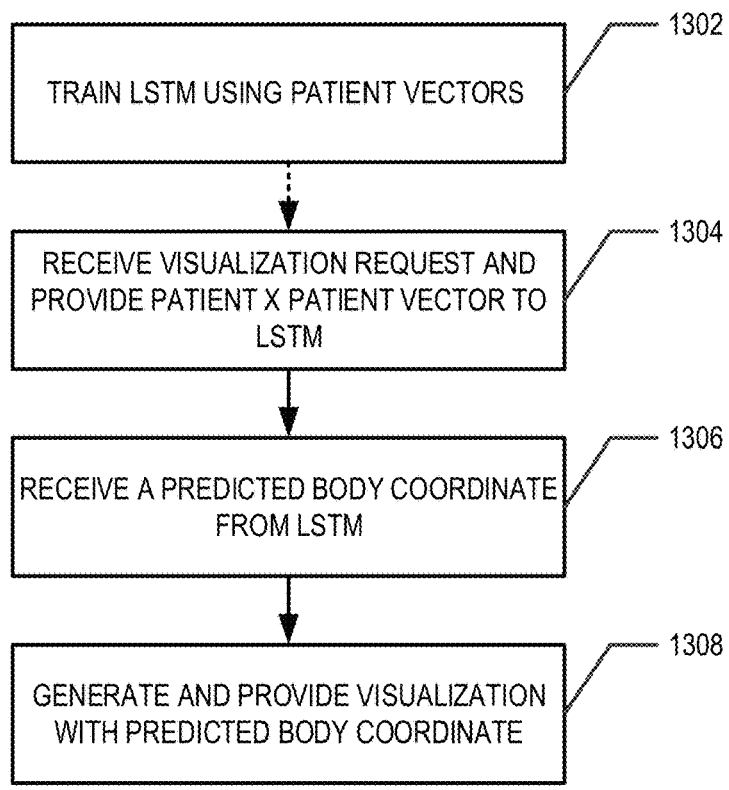

FIG. 4 provides a flowchart illustrating example procedures, processes, and/or operations performed by a visualization computing entity to provide a visualization of a past, current, and/or predicted future medical state of a patient, in accordance with an example embodiment of the present invention;

FIG. 5 provides a flowchart illustrating example procedures, processes, and/or operations performed by a visualization computing entity to assign a set of body coordinates to teach medical code of a set of medical codes, in accordance with an example embodiment of the present invention;

FIG. 6 is an example code chart, in accordance with an example embodiment of the present invention;

FIG. 7 provides a flowchart illustrating example procedures, processes, and/or operations performed by a visualization computing entity to provide a visualization of a past medical state of a patient, in accordance with an example embodiment of the present invention;

FIG. 8 provides a flowchart illustrating example procedures, processes, and/or operations performed by a user computing entity to provide an interactive user interface for displaying a visualization of a past, current, or predicted future medical state of a patient, in accordance with an example embodiment of the present invention;

FIGS. 9A and 9B illustrate example views of an interactive user interface, in accordance with an example embodiment of the present invention;

FIG. 10 provides a flowchart illustrating example procedures, processes, and/or operations performed by a visualization computing entity to provide patient information corresponding to a cohort associated with the patient, in accordance with an example embodiment of the present invention;

FIG. 11 provides a flowchart illustrating example procedures, processes, and/or operations performed by a visualization computing entity to provide a visualization of a current medical state comprising a point or zone corresponding to a suggested medical code, in accordance with an example embodiment of the present invention;

FIG. 12 provides a flowchart illustrating example procedures, processes, and/or operations performed by a visualization computing entity to provide a visualization of a current medical state comprising a point or zone corresponding to a suggested medical code, in accordance with another example embodiment of the present invention; and FIG. 13 provides a flowchart illustrating example procedures, processes, and/or operations performed by a visualization computing entity to provide a visualization of a predicted medical state of a patient, in accordance with an example embodiment of the present invention.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. General Overview

In various embodiments, methods, systems, apparatuses, computer program products, and/or the like are provided for providing visualizations of the past, current, and/or predicted future medical states of one or more patients. In an example embodiment, visualization comprises a graphical representation of a human body and one or more points and/or zones located on and/or mapped to the graphical representation of the human body. Each point and/or zone is mapped to a location on the graphical representation of the human body via a set of body coordinates and corresponds to a medical code. In various embodiments, a past, current, and/or predicted future medical state is represented by one or more sets of body coordinates. Each set of body coordinates corresponds to a medical code and indicates a location on a model human body. In various embodiments, the location on the model human body corresponds to a body part that is associated with and/or corresponds to the corresponding medical code. In various embodiments, providing the visualization of a current medical state for a patient comprises determining a suggested medical code for the patient based on the set(s) of body coordinates representing a past and/or present medical state of the patient and/or current symptoms of the patient. In various embodiments, providing the visualization of a predicted future medical state for a patient comprises determining a predicted medical code and/or predicted body part for the patient based on the set(s) of body coordinates representing a past and/or present medical state of the patient. In various embodiments, one or more cohorts corresponding to the patient may be determined based on the set(s) of body coordinates representing a past, current, and/or predicted future medical state of the patient. In an example embodiment, cohort specific information/data may be provided to the patient based on a cohort identified for the patient.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

Figure 1:
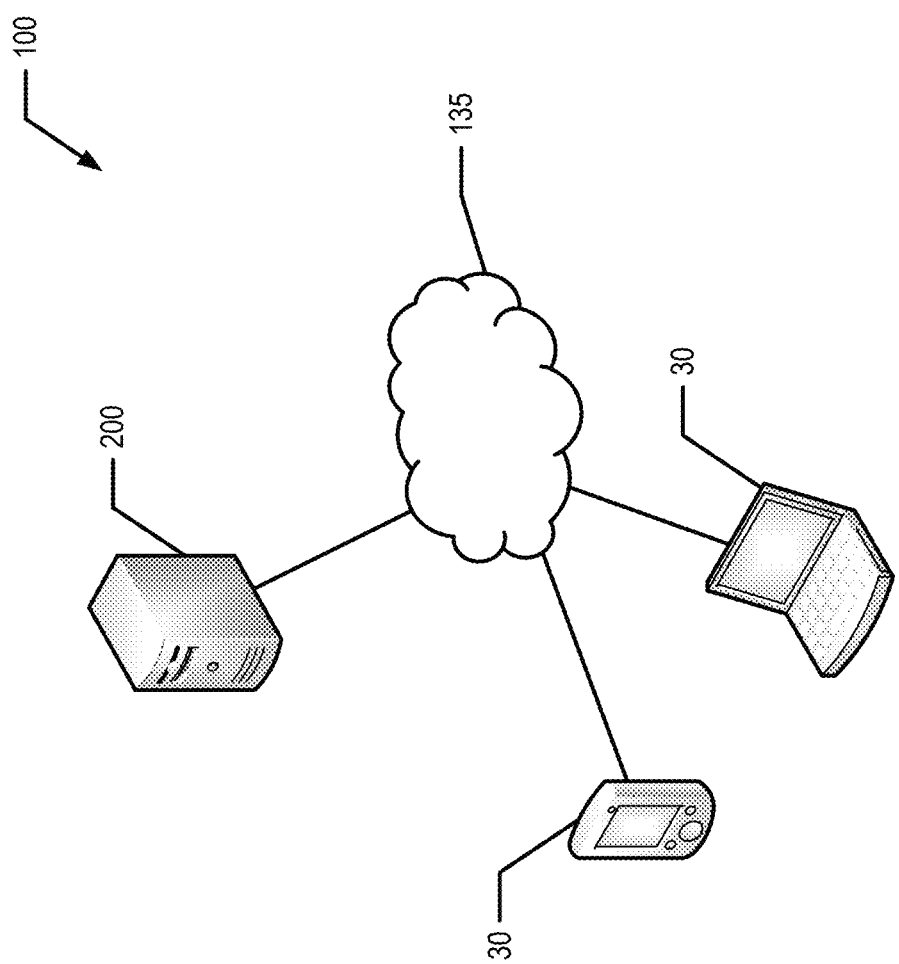
FIG. 1 is a diagram of a system that can be used to practice various embodiments of the present invention.

FIG. 1 provides an illustration of a system 100 that can be used in conjunction with various embodiments of the present invention. As shown in FIG. 1, the system 100 may comprise one or more visualization computing entities 200, one or more user computing entities 30, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Visualization Computing Entity

Figure 2:
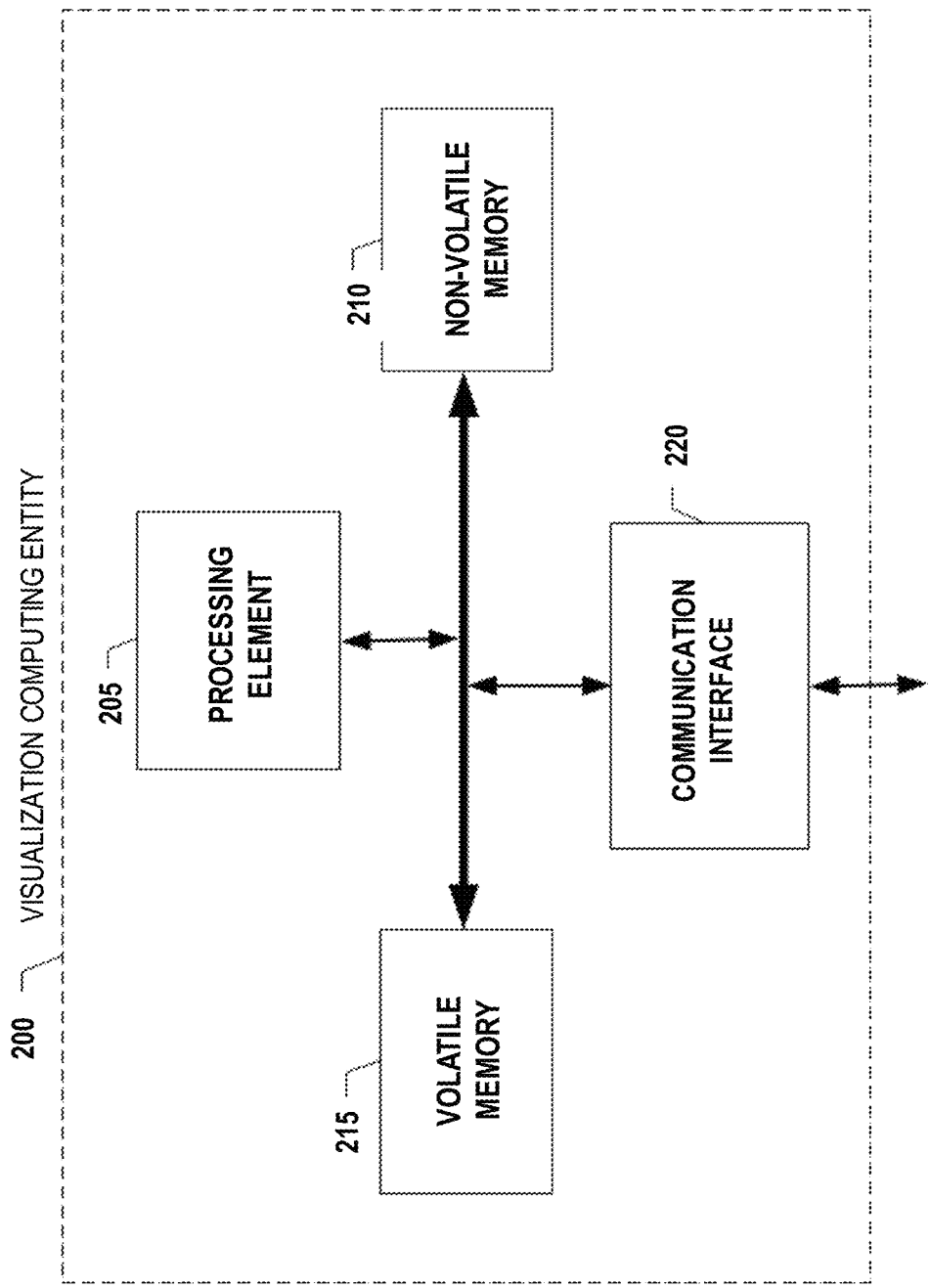
FIG. 2 is a schematic of a visualization computing entity in accordance with certain embodiments of the present invention.

FIG. 2 provides a schematic of a visualization computing entity 200 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the visualization computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. For instance, the visualization computing entity 200 may communicate with other visualization computing entities 200, one or more user computing entities 30, and/or the like.

As shown in FIG. 2, in one embodiment, the visualization computing entity 200 may include or be in communication with one or more processing elements 205 (also referred to as processors, processing circuitry, and/or similar terms used herein interchangeably) that communicate with other elements within the visualization computing entity 200 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the visualization computing entity 200 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In one embodiment, the visualization computing entity 200 may further include or be in communication with volatile media (also referred to as volatile storage, memory, memory storage, memory circuitry and/or similar terms used herein interchangeably). In one embodiment, the volatile storage or memory may also include one or more volatile storage or memory media 315 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 305. Thus, the databases, database instances, database management system entities, data, applications, programs, program modules, scripts, source code, object code, byte code, compiled code, interpreted code, machine code, executable instructions, and/or the like may be used to control certain aspects of the operation of the visualization computing entity 200 with the assistance of the processing element 205 and operating system.

As indicated, in one embodiment, the visualization computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. For instance, the visualization computing entity 200 may communicate with computing entities or communication interfaces of other visualization computing entities 200, user computing entities 30, and/or the like.

As indicated, in one embodiment, the visualization computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the visualization computing entity 200 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol. The visualization computing entity 200 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the visualization computing entity's 200 components may be located remotely from other visualization computing entity 200 components, such as in a distributed system. Furthermore, one or more of the components may be aggregated and additional components performing functions described herein may be included in the visualization computing entity 200. Thus, the visualization computing entity 200 can be adapted to accommodate a variety of needs and circumstances.

b. Exemplary User Computing Entity

Figure 3:
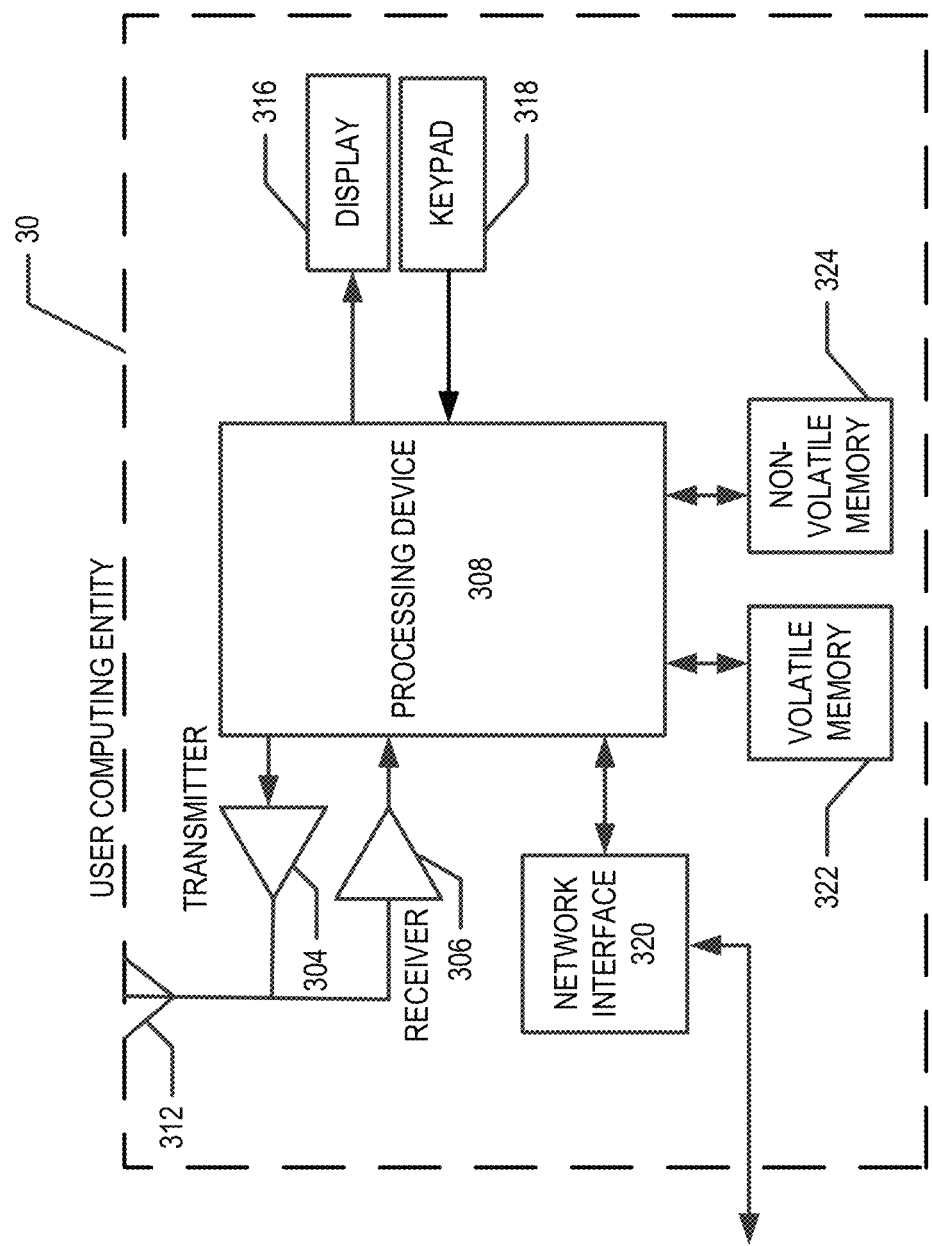
FIG. 3 is a schematic of a user computing entity in accordance with certain embodiments of the present invention.

FIG. 3 provides an illustrative schematic representative of user computing entity 30 that can be used in conjunction with embodiments of the present invention. As shown in FIG. 3, a user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a visualization computing entity 200, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing device 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the user computing entity's 30 position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise and/or be in communication with a user interface device comprising one or more user output interfaces and/or devices (e.g., a display 316 and/or speaker/speaker driver coupled to a processing element 308) and one or more user input interfaces and/or devices (e.g., a touch screen, keyboard, mouse, and/or microphone coupled to a processing element 308). For example, the user output interface may be configured to provide an application, browser, interactive user interface, dashboard, webpage, and/or similar words used herein interchangeably executing on and/or accessible via the user computing entity 30 to cause display or audible presentation of information/data (e.g., a visualization of a past, current, and/or predicted future medical state of a patient) and for user interaction therewith via one or more user input interfaces. The user input interface can comprise any of a number of devices allowing the user computing entity 30 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

As indicated, in one embodiment, the user computing entity 30 may also include one or more communications interfaces, such as transmitter/receiver 304/306 and/or network interface 320 for communicating with various computing entities, such as by communicating data, content, information, and/or similar terms used herein interchangeably that can be transmitted, received, operated on, processed, displayed, stored, and/or the like. For instance, the user computing entity 30 may communicate with computing entities or communication interfaces of visualization computing entities 200, other user computing entities 30, and/or the like.

As indicated, in one embodiment, the user computing entity 30 may also include one or more communications interfaces (e.g., transmitter/receiver 304/306 and/or network interface 320) for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as FDDI, DSL, Ethernet, ATM, frame relay, DOC SIS, or any other wired transmission protocol. Similarly, the user computing entity 30 may be configured to communicate via wireless external communication networks using any of a variety of protocols, such as GPRS, UMTS, CDMA2000, 1xRTT, WCDMA, GSM, EDGE, TD-SCDMA, LTE, E-UTRAN, EVDO, HSPA, HSDPA, Wi-Fi, Wi-Fi Direct, WiMAX, UWB, IR protocols, NFC protocols, Wibree, Bluetooth protocols, wireless USB protocols, and/or any other wireless protocol. The user computing entity 30 may use such protocols and standards to communicate using BGP, DHCP, DNS, FTP, HTTP, HTTP over TLS/SSL/Secure, IMAP, NTP, SMTP, Telnet, TLS, SSL, IP, TCP, UDP, DCCP, SCTP, HTML, and/or the like.

c. Exemplary Networks

In one embodiment, any two or more of the illustrative components of the architecture of FIG. 1 may be configured to communicate with one another via respective communicative couplings to one or more networks 135. The networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

IV. Exemplary System Operation

Medical information/data (and similar words used herein interchangeably) is often encoded using medical codes. For example, procedure codes, diagnostic codes, prescription or drug codes, equipment codes, revenue codes, place of service codes, and/or the like may be used to encode various portions of an instance of medical information/data. As medical codes are non-interpretable, alpha-numeric strings, the medical codes themselves fail to provide a body-based interpretation of the medical information/data. Various embodiments of the present invention provide a spatial, body-based interpretation and/or visualization of medical information/data. In various embodiments, a body model is generated and used to assign a set of body coordinates to each medical code of a plurality of medical codes. For example, a medical code may be assigned a set of body coordinates that correspond to the location of a body part in the body model, where the body part corresponds to a body part name extracted from the description of the medical code. Medical information/data corresponding to a patient and the sets of body coordinates assigned to medical codes encoding the medical information/data may be used to generate, provide, and/or display a visualization of a past, current, and/or predicted future medical state of the patient.

In various embodiments, a medical state is represented by one or more sets of body coordinates. In various embodiments, a visualization comprises a graphical representation of human body, for example, generated based on the body model. In various embodiments, the visualization further comprises one or more points and/or zones located on the graphical representation of the human body and that correspond to and/or provide a graphical representation of at least one of the one or more sets of body coordinates that represent the patient's medical state. In various embodiments, a past medical state is represented by one or more sets of body coordinates that correspond to medical codes that encode at least a portion of a patient's medical history.

In various embodiments, a current medical state is represented by one or more sets of body coordinates that each correspond to a suggested medical code. A suggested medical code is identified and/or determined based on sets of body coordinates that correspond to medical codes that encode at least a portion of a patient's medical history and/or current patient symptoms. A current medical state may include one or more sets of body coordinates that correspond to medical codes that encode at least a portion of a patient's medical history in addition to the set(s) of suggested body coordinates. In various embodiments, at least some of the sets of body coordinates corresponding to medical codes that encode at least a portion of a patient's medical history and/or current patient symptoms are combined and/or aggregated to generate a set of suggested body coordinates.

In various embodiments, a future medical state is represented by one or more sets of predicted body coordinates that each correspond to a predicted medical code. A set of predicted body coordinates and/or a predicted medical code are determined based on one or more sets of body coordinates that correspond to medical codes that encode at least a portion of a patient's medical history and, in an example embodiment, is determined by a trained model. For example, the trained model may be a neural network, deep net, and/or the like. For example, the trained model may be a long short term model (LSTM). In various embodiments, the trained model is trained using a plurality of vectors comprising one or more sets of body coordinates that correspond to medical codes that encode at least a portion of a patient's medical history for each patient of a population of patients. A current medical state may include one or more sets of body coordinates that correspond to medical codes that encode at least a portion of a patient's medical history in addition to the set(s) of predicted body coordinates. In an example embodiment, a set of predicted body coordinates corresponds to a time period. For example, it may be predicted that in the next three months, next six months, next year, next two years, next five years, next ten years, and/or the like, a patient will experience a medical situation corresponding to the set of predicted body coordinates. In an example embodiment, the time period may be determined by the trained model and/or may be provided as an input to the trained model. For example, the trained model may be configured to identify one or more sets of predicted body coordinates for a patient and corresponding time periods corresponding to when it is expected and/or likely that the patient would experience a medical situation corresponding to each set of predicted body coordinates. In another example, the trained model may be configured to identify one or more sets of predicted body coordinates that a patient is expected and/or likely to experience a medical situation corresponding to within a predetermined time period.

In various embodiments, a set of body coordinates is a three dimensional set of coordinates that corresponds to location on a body model and/or graphical representation of a human body corresponding to the body model. In various embodiments, the body model is a three dimensional body model. In an example embodiment, the body model is a two dimensional body model. For example, the z-coordinate may be introduced as a visualization tool for providing the graphical representation of the human body rather than as a part of the body model itself. For example, in an example embodiment, the x-coordinate corresponds to the left-right axis of the body model. In an example embodiment, the x-axis runs left to right across the human body model, as shown in FIG. 9B. For example, the x-axis may be perpendicular to a line between the naval of the body model and the midpoint between the eyes of the body model, in an example embodiment. For example, the x-axis may be the left-right axis of the body model. In an example embodiment, the y-coordinate may correspond to the height of the body model. For example, the y-coordinate may indicate the height of a body part on the body model above the ground. In another example, the y-coordinate may indicate the height of a body part on the body model with midpoint along the height of the body model (e.g., the height of a body part above or below the naval of the body model). For example, the y-axis may be the craniocaudal axis of the body model. In an example embodiment, the z-coordinate corresponds to the depth of a body part between the front and the back of the body model. For example, the z-axis may be the dorsoventral axis of the body model.

FIG. 4 provides a flowchart illustrating various processes, procedures, operations, and/or the like performed by the visualization computing entity 200. For example, starting at step/operation 402, the visualization computing entity 200 maps each of a plurality of medical codes to a set of body coordinates to generate, for example, a code chart 600 (see FIG. 6), code database, code table, and/or the like. For example, the code chart 600, code database, code table, and/or the like may be used to associate a set of body coordinates to a medical code. At step/operation 404, the mapping of the plurality of medical codes to the sets of body coordinates (e.g., the code chart 600) is used to provide a visualization of a past, current, and/or predicted future medical state of a particular patient. Optionally, at step/operation 406, in an example embodiment, cohort specific information/data is provided based on a cohort associated with the patient. Various features of the present invention are described in more detail below with respect to FIGS. 5-13.

a. Assigning Sets of Body Coordinates to Medical Codes

FIG. 5 provides a flowchart of example processes, procedures, and/or operations for assigning a set of body coordinates to a medical code, in accordance with an example embodiment, for example, to generate a code chart 600, and/or the like. In various embodiments, a set of body coordinates is a three dimensional (e.g., x, y, z) set of coordinates in a coordinate system corresponding to a body model and/or a graphical representation of the body model (e.g., a body model that has been scaled based on one or more characteristics of a patient). Starting at step/operation 502, a medical code list is accessed. The medical code list comprises a plurality of medical codes and corresponding text descriptions. For example, the text description corresponding to a medical code may be the official textual description of the medical code. In various embodiments, the medical code list is accessed from a medical code database, table, and/or the like. For example, the medical code list may comprise a plurality of ICD-10 codes and their corresponding text descriptions. In various embodiments, the medical code list is accessed by the visualization computing entity 200 from memory 210, 215 and/or via communication interface 220.

At step/operation 504, body part names are extracted from the text descriptions corresponding to the plurality of medical codes. For example, the visualization computing entity 200 extracts body part names from the text descriptions corresponding to the plurality of medical codes. For example, a medical term dictionary, anatomy dictionary, and/or the like may be accessed to identify and extract body part names from the text descriptions. In an example embodiment, a general term dictionary, preposition dictionary, verb dictionary, adjective dictionary, adverb dictionary, and/or the like such that terms in the text descriptions that are not nouns may be identified. The body part names may then be extracted from the remaining nouns of the text descriptions.

At step/operation 506, a master list of body part names is generated from the body part names extracted from the text descriptions. For example, the visualization computing entity generates a master list of body part names from the body part names extracted from the text descriptions. For example, the master list of body part names may be a list of unique body part names generated from the body part names extracted from the text descriptions. For example, the master list of body part names may be generated by adding each body part name extracted from the text descriptions to a list and then filtering the list to remove duplicates.

In an example embodiment, the process continues from step/operation 506 to step/operation 508. At step/operation 508, one or more clinicians may review the master list of body part names and assign a set of body part coordinates to each body part name. The set of body part coordinates assigned to a body part name corresponds to a point and/or zone in a human body model corresponding to the body part identified by the body part name. For example, the visualization computing entity 200 may be operated by one or more clinicians (e.g., receive user input via a user interface and/or user input device) and/or receive information/data from one or more user computing entities 30 (e.g., corresponding to user input provided via a user input device of the user computing entity 30) that indicates a set of body coordinates to be assigned to a body part name. The visualization computing entity 200 then stores the set of body coordinates in association with the body part name.

In an example embodiment, a set of body part coordinates may be assigned to each body part name of the master list of body parts in an automated and/or partially automated manner. In such embodiments, the process may continue from step/operation 506 to step/operation 510. At step/operation 510, a set of anatomy maps are gathered and/or accessed. For example, one or more digital anatomy maps may be accessed. In an example embodiment, one or more anatomy maps may be digitized and the digitized anatomy map may be accessed. In various embodiments, an anatomy map is a graphical representation of at least a portion of a body with one more body parts labeled. For example, the graphical representation of at least a portion of a body may have one or more body parts labeled with body part text. For example, the visualization computing entity 200 may access one or more anatomy maps. In various embodiments, one or more of the anatomy maps are two dimensional anatomy maps. In various embodiments, one or more of the anatomy maps are three dimensional anatomy maps.

At step/operation 512, words are identified on the anatomy maps. For example, natural language processing (NLP), optical character recognition (OCR), and/or the like may be used to identify the words on the anatomy maps. For example, the visualization computing entity 200 may identify the words on each of the anatomy maps. The words identified on the anatomy maps may then be filtered to identify body part text identifying one or more body parts shown on the corresponding anatomy map. For example, the visualization computing entity 200 may filter the words identified on each of the anatomy maps to identify body part text.

At step/operation 514, the body part text identified from the words of the anatomy maps are matched to the body part names of the master list of body part names. For example, the visualization computing entity 200 may match the body part names of the master list of body part names to the body part text identified from the anatomy maps. For example, body part text that is the same or generally the same as a body part name may be matched to one another. For example, if the body part text is "Knee Cap" and the body part name is "knee cap," the body part text and the body part name are matched. In another example, an anatomy dictionary may be used to identify body part text that is different from the body part name of the mater list of body part names but that refers to the same body part. For example, the body part text "skull" may be matched to the body part name "cranium."

At step/operation 516, the body model is built, generated, and/or created by assigning and/or associating a set of body coordinates to each body part name of the master list of body part names based on the anatomy maps. For example, the visualization computing entity 200 may build, generate, and/or create a body model. For example, the visualization computing entity 200 may assign and/or associate a set of body coordinates to each body part name of the master list of body parts based on the anatomy maps to provide the body model. For example, the set of body coordinates assigned and/or associated with a body part name correspond to the location of the corresponding body part in a body model generated based on one of the anatomy maps and/or by combining and/or aggregating a plurality of anatomy maps.

For example, a first body part name is matched to a first body part text on a first anatomy map. Based on the first anatomy map and the label corresponding to the first body part text, a point or zone corresponding to the first body part corresponding to the first body part text is determined and/or identified. A first set of body part coordinates is then determined based on location of the point and/or zone corresponding to the first body part in the first anatomy map. In another example, a second body part name is matched to second body part text on a second anatomy map and third body part text on a third anatomy map. Based on the second anatomy map and the label corresponding to the second body part text, a point or zone corresponding to the second body part corresponding to the second body part text is determined and/or identified. A second set of body part coordinates is then determined based on location of the point and/or zone corresponding to the second body part in the second anatomy map. Similarly, based on the third anatomy map and the label corresponding to the third body part text, a point or zone corresponding to the second body part corresponding to the third body part text is determined and/or identified. A third set of body part coordinates is then determined based on location of the point and/or zone corresponding to the second body part in the third anatomy map. The second and third sets of body coordinates may then be combined, averaged, or aggregated to determine a set of body coordinates for the second body part.

In an example embodiment, if each anatomy map used that includes body part text matched to a body part name is a three dimensional anatomy map, the set of body part coordinates may be three dimensional (e.g., the set of body coordinates may only include x- and y-coordinates or the z-coordinate may be set to zero or another pre-set and/or arbitrary value). In an example embodiment, a clinician operating the visualization computing entity 200 and/or a user computing entity 30 may provide input (e.g., via a user input device) to provide a z-coordinate corresponding to the body part such that the set of body part coordinates is a three dimensional set of coordinates. If at least one anatomy map used that includes body part text matched to a body part name is a three dimensional anatomy map, the set of body part coordinates are three dimensional coordinates (e.g., includes x-, y-, and z-coordinates).

At step/operation 518, a set of body coordinates is assigned to each medical code. For example, the visualization computing entity 200 may assign a set of body coordinates to each medical code. For example, a code chart 600 may be generated that encodes the body model. FIG. 6 shows an example code chart 600. In an example embodiment, a code chart 600 is table comprising a column of medical codes, a column of the body part names extracted from the text description corresponding to the medical code, and a column that includes the set of body part coordinates assigned to the medical code. In an example embodiment, the code chart 600 may include a column that comprises the text description of the corresponding medical code and/or other information/data corresponding to one or more of the medical codes. For example, to assign a set of body coordinates to a medical code, the body part name corresponding to the medical code is identified and set of body coordinates assigned to corresponding body part name is assigned to the medical code.

b. Providing a Visualization of a Past Medical State of a Patient

FIG. 7 provides a flowchart illustrating example procedures, processes, and/or operations for providing a visualization of a past medical state of a patient, in accordance with an example embodiment of the present invention. In various embodiments, a past medical state of a patient is represented by a vector of sets of body coordinates where each set of body coordinates corresponds to medical code in the patient's medical history, medical file, and/or the like. For example, a past medical state of the patient may only include sets of body coordinates that correspond to medical codes that have already been applied to the patient (e.g., diagnosis codes for diagnoses of the patient that have already been made).

Starting at step/operation 702, a visualization request is received. For example, the visualization computing entity 200 may receive a visualization request. For example, a user computing entity 30 may generate and provide (e.g., transmit) a visualization request such that the visualization computing entity 200 receives the visualization request. In various embodiments, the visualization request comprises a patient identifier (e.g., a patient's name, birthdate, all or last four digits of a social security number, or other patient identifier). In various embodiments, the visualization request comprises a visualization type (e.g., a visualization of a past, current, or predicted future medical state of the patient identified by the patient identifier provided in the visualization request). In an example embodiment, the visualization request may comprise filter information/data that indicates which portion(s) of the patient's medical history should be visualized. For example, the filter information/data may indicate that the visualization should only include points and/or zones corresponding to sets of body coordinates that correspond to the last five years, last ten years, and/or the like of the patient's medical history. In another example, the filter information/data may indicate that the visualization should only include points and/or zones corresponding to sets of body coordinates that correspond to a particular diagnosis and complications and/or related diagnoses. For example, if a patient has type two diabetes, the filter information/data may indicate that the visualization should only provide information/data corresponding to diagnoses related to type two diabetes (e.g., hypertension, type two diabetes related nerve problems, and/or the like).

At step/operation 704, responsive to receiving and processing the visualization request, medical codes are extracted from the patient's medical history. For example, the visualization computing entity 200 may securely access the patient's medical history (e.g., from memory 210, 215 and/or a data store stored in another computer-readable memory) and extract medical codes from the patient's medical history. In an example embodiment, only medical codes that satisfy the filter information/data are extracted from the patient's medical history. In another example embodiment, all of the medical codes are extracted from the patient's medical history and then the extracted medical codes are filtered based on the filter information/data.

At step/operation 706, a set of body coordinates is identified for each of the extracted and/or filtered medical codes corresponding to the patient's medical history (e.g., determined at step/operation 704). For example, the visualization computing entity may identify a set of body coordinates for each of the extracted and/or filtered medical codes corresponding to the patient's medical history. For example, the code chart 600 may be accessed to identify and/or determine a set of body coordinates for each of the extracted and/or filtered medical codes corresponding to the patient's medical history. In an example embodiment, a vector comprising the sets of body coordinates corresponding to the extracted and/or filtered medical codes corresponding to the patient's medical history is generated and/or formed.

At step/operation 708, the visualization is generated. For example, the visualization computing entity 200 may generate the visualization. For example, the graphical representation of the human body may be generated. In an example embodiment, generating the graphical representation of the human body comprising scaling the body model based on one or more patient characteristics (e.g., male/female, height, weight, waist measurement, hip measurement, eye color, hair color, amputation, body type/shape category, and/or other patient characteristic). For example, the sets of body coordinates are generated based on the body model and/or correspond to locations on a body model. The body model may be scaled based on one or more patient characteristics and the sets of body coordinates may be transformed based on the scaling of the body model. For example, the sets of body coordinates may be determined based on a standardized body model and to generate the visualization, the sets of body coordinates and the body model may be transformed to provide an individualized visualization for a patient. For example, if the body model is scaled based on the patient's height, the y-coordinate of each set of body characteristics may be transformed based on the scaling of the body model based on the patient's height. In an example embodiment, generating the visualization comprises identifying, marking, changing the coloring, and/or the like of the points and/or zones of the graphical representation of the human body located at and/or corresponding to the sets of body coordinates identified for the extracted and/or filtered medical codes corresponding to the patient's medical history. For example, the body part corresponding to the location indicated by a set of body coordinates corresponding to an extracted and/or filtered medical code may be highlighted on the graphical representation of the human body (e.g., the body part may be shown and/or may be shown in a color coded manner, a marker may be positioned at the point and/or zone indicated by the set of body coordinates and/or the like). For example, FIG. 9B shows an example of a visualization 952 that has been rendered and displayed on a display 316 of a user computing entity 30. Markers 956A, 956B show the location of body parts on the graphical representation of the human body 954 indicated by the set of body coordinates corresponding to the extracted and/or filtered medical codes corresponding to the patient's medical history. In various embodiments, generating the visualization may comprise adding one or more labels 958 (e.g., 958A, 958B) to the graphical representation of the human body 954. For example, a label 958 may provide information/data corresponding to a marked point or zone. For example, a label 958 may include the medical code that corresponds to the set of body coordinates that identified the marked point and/or zone, a text description of the medical code that corresponds to the set of body coordinates that identified the marked point and/or zone, the date that a diagnosis corresponding to the point and/or zone was made, healthcare provider notes corresponding to the diagnosis corresponding to the point and/or zone, and/or the like.

At step/operation 710, the visualization is provided for rendering and displaying. For example, the visualization computing entity 200 may provide (e.g., transmit) the visualization such that a use computing entity 30 receives the visualization such that the user computing entity 30 may render and display the visualization. In an example embodiment, the visualization may be compressed before the visualization is provided. In an example embodiment, the visualization is provided such that the user computing entity 30 that generated and provided the visualization request receives the visualization. In an example embodiment, the visualization may be encoded in a secure manner for transmission.

As described with respect to FIG. 7, the visualization computing entity 200 generates the visualization. However, in an example embodiment, the user computing entity 30 may have access to the patient's medical record and the code chart 600 and the user computing entity 30 may generate the visualization.

c. Displaying a Visualization of Medical State of a Patient

FIG. 8 provides a flowchart illustrating example procedures, processes, and/or operations performed by a user computing entity to provide an interactive user interface for displaying a visualization of a past, current, or predicted future medical state of a patient, in accordance with an example embodiment of the present invention. Starting at step/operation 802, the user computing entity 30, operated by a user, executes computer program code to provide an interactive user interface. For example, the memory 322, 324 may store computer program code that, when executed by the processing device 308, causes the user computing entity 30 to provide an interactive user interface 900 via the display 316, as shown in FIG. 9A. In various embodiments, the user is a healthcare professional, a patient, and/or an agent of the patient. The user may interact with the interactive user interface 900 via a user input device (e.g., mouse, keyboard, touchscreen, and/or the like) to provide input providing user credentials, identifying the user, and/or indicating that the user would like to view a visualization of a medical state of the patient. The user may provide input selecting a selectable element 902. For example, the interactive user interface 900 may provide a selectable element 902A corresponding to requesting a visualization of a past medical state of the patient, a selectable element 902B corresponding to a predicted future medical state of the patient, a selectable element 902C corresponding to cohort information/data and/or a visualization related to cohort information/data, a selectable element 902D corresponding to a current medical state of the patient, and/or the like. In an example embodiment, the interactive user interface 900 may further comprise fields and/or selectable elements for a user to enter filter information/data, current symptoms (e.g., via symptom field 904), and/or the like.

Continuing with FIG. 8, at step/operation 804, responsive to receiving and/or processing user input (e.g., received via a user input device), a visualization request is generated and provided. For example, the visualization request may encode and/or include a patient identifier, filter information/data, a visualization type, current symptoms (if any were provided), and/or the like. For example, the user computing entity 30 may generate a visualization request based on the received user input and provide (e.g., transmit) the visualization request. For example, the user computing entity 30 may provide the visualization request such that the visualization computing entity 200 receives the visualization request.

At step/operation 806, the visualization is received. For example, the visualization computing entity 200 may generate and provide a visualization responsive to the visualization request and the user computing entity 30 may receive the visualization. At step/operation 808, the visualization is rendered. For example, the user computing entity 30 may process the visualization and render the visualization. At step/operation 810, the visualization is displayed via the interactive user interface. For example, the user computing entity 30 may cause the rendered visualization to be displayed via the display 316.

FIG. 9B shows an example interactive user interface 900 displaying a visualization 952. The visualization 952 comprises a graphical representation of a human body 954 and markers 956 (e.g., 956A, 956B) identifying and/or marking points and/or zones of the graphical representation of the human body 954 at the location of and/or corresponding to body parts identified by the sets of body coordinates corresponding to the extracted and/or filtered medical codes of the patient's medical record. In an example embodiment, one or more markers 956 may identify and/or mark points and/or zones corresponding to suggested body coordinates and/or medical codes. In an example embodiment, one or more markers 956 may identify and/or mark points and/or zones corresponding to predicted future sets of body coordinates and/or medical codes. In an example embodiment, one or more markers 956 may identify and/or mark points and/or zones corresponding to a cohort associated with the patient. In various embodiments, the visualization 952 comprises one or more labels 958. For example, information/data corresponding to one or more points and/or zones and/or the corresponding suggested, predicted future, and/or patient medical record indicated medical code is provided by one or more labels 958. For example, a label 958 may include the medical code that corresponds to the set of body coordinates that identified the marked point and/or zone, a text description of the medical code that corresponds to the set of body coordinates that identified the marked point and/or zone, the date that a diagnosis corresponding to the point and/or zone was made, healthcare provider notes corresponding to the diagnosis corresponding to the point and/or zone, and/or the like.

d. Identifying Cohorts of Patients

In various embodiments, cohorts of patients that have at least one similarity in their medical records may be identified based on vectors of sets of body coordinates corresponding to each patient. FIG. 10 provides a flowchart illustrating example procedures, processes, and/or operations to provide patient information corresponding to a cohort associated with the patient, in accordance with an example embodiment of the present invention. Starting at step/operation 1002, a patient vector is determined for each patient in a population of patients. For example, the visualization computing entity may determine a patient vector for each patient in a population of patients. A patient vector is a vector or array of sets of body coordinates corresponding to medical codes extracted from a patient's medical record. For example, a patient vector may be generated for a patient by accessing the patient's medical record, extracting medical codes from the patient's medical record, identifying a set of body coordinates for each of the extracted medical codes, and forming the patient vector by putting the identified sets of body coordinates into an array or vector.

At step/operation 1004, one or more cohorts of patients are identified from the population of patients based on the corresponding patient vectors. For example, the visualization computing entity 200 may identify one or more cohorts from the population of patients based on the patients' corresponding patient vectors. In an example embodiment, clusters of patients having one or more similar body coordinates may be identified. For example, patients corresponding to patient vectors that include sets of body coordinates corresponding to the left or right knee may be identified as a cohort. In an example embodiment, clusters of patients having similar body coordinate patterns may be identified. For example, patients corresponding to patient vectors that include both sets of body coordinates corresponding the left or right knee and sets of body coordinates corresponding to points and/or zones in the lower back may be identified as a cohort.

In various embodiments, each cohort may be assigned a cohort identifier. At step/operation 1006, if a patient is determined to be part of a first cohort, a cohort identifier configured to identify the first cohort is added to a patient file corresponding to the patient. In an example embodiment, the visualization computing entity 200 may add the cohort identifier to the patient file. For example, the patient file may be the patient's medical record or may be another file, profile, and/or account corresponding to the patient and accessible to and/or stored by the visualization computing entity 200.

At step/operation 1008, cohort specific information/data is provided for provision to the patient based on the cohort identifier stored in the patient file corresponding to the patient. For example, the visualization computing entity 200 may provide cohort specific information/data and the user computing entity 30 may receive the cohort specific information/data and provide the cohort specific information/data to a user (e.g., via a user output device). For example, when a user access the interactive user interface corresponding to a patient, a cohort associated with the patient may be identified (based on the cohort identifier(s) stored as part of the corresponding patient file). Based on the identified cohort(s) associated with the patient one or more instances of cohort specific information/data may be identified and provided for provision to the user. For example, if the patient is associated with a cohort corresponding to left or right knees, the cohort specific information/data may be related to a new type of new knee replacement implant, an advertisement for a knee brace, and/or the like.

e. Providing a Visualization of a Current Medical State Based on a Cohort

In various embodiments, a visualization of a current medical state of a patient may be provided. In various embodiments, a current medical state of a patient is represented by at least one suggested set of body coordinates. In an example embodiment, a current medical state of a patient may be further represented by one or more sets of body coordinates corresponding to medical codes extracted from the patient's medical record. FIG. 11 provides a flowchart illustrating example procedures, processes, and/or operations to provide a visualization of a current medical state comprising a point or zone corresponding to a suggested medical code determined based on a cohort, in accordance with an example embodiment of the present invention.

In various embodiments, a visualization request for a visualization of a current medical state of a patient is received. For example, the visualization computing entity 200 may receive a visualization request. For example, a user computing entity 30 may generate and provide (e.g., transmit) a visualization request such that the visualization computing entity 200 receives the visualization request. In various embodiments, the visualization request comprises a patient identifier (e.g., a patient's name, birthdate, all or last four digits of a social security number, or other patient identifier). In various embodiments, the visualization request indicates that the desired visualization is that of a current medical state of the patient. In an example embodiment, the visualization request comprises one or more current symptoms. For example, the visualization request may comprise a description and/or medical codes corresponding to one or more symptoms currently being experienced by the patient. In an example embodiment, the visualization request may comprise filter information/data that indicates which portion(s) of the patient's medical history should be visualized. For example, the filter information/data may indicate that the visualization should only include points and/or zones corresponding to sets of body coordinates that correspond to the last five years, last ten years, and/or the like of the patient's medical history. In another example, the filter information/data may indicate that the visualization should only include points and/or zones corresponding to sets of body coordinates that correspond to a particular diagnosis and complications and/or related diagnoses. For example, if a patient has type two diabetes, the filter information/data may indicate that the visualization should only provide information/data corresponding to diagnoses related to type two diabetes (e.g., hypertension, type two diabetes related nerve problems, and/or the like).

At step/operation 1102, responsive to receiving and processing the visualization request, a patient vector and/or current symptom vector is generated for the patient. For example, the visualization computing entity 200 may generate a patient vector and/or current symptom vector for the patient. For example, medical codes may be extracted from the patient's medical history. For example, the visualization computing entity 200 may securely access the patient's medical history (e.g., from memory 210, 215 and/or a data store stored in another computer-readable memory) and extract medical codes from the patient's medical history. In an example embodiment, only medical codes that satisfy the filter information/data are extracted from the patient's medical history. In another example embodiment, all of the medical codes are extracted from the patient's medical history and then the extracted medical codes are filtered based on the filter information/data. A set of body coordinates is determined and/or identified (e.g., using the code chart 600) for each extracted and/or filtered medical code and the determined and/or identified set of body coordinates are used to form a patient vector for the patient. In an example embodiment, one or more body coordinates corresponding to the current symptoms are determined. For example, if the patient reports sinus headaches as a current symptom, a set of body coordinates corresponding to a headache and/or the sinuses may be identified and/or determined. A current symptoms vector is generated and/or formed by adding the sets of body coordinates determined and/or identified based on the current symptoms provided in the visualization request to a vector and/or array.

At step/operation 1104, a cohort for the patient is identified based on the patient vector, the current symptoms vector, and/or a cohort identifier stored in the patient file. For example, the visualization computing entity 200 identifies a cohort for the patient based on the patient vector, the current symptoms vector, and/or a cohort identifier stored in the patient file. For example, the cohort for the patient may be determined based on the patient vector and/or current symptoms vector as described above with respect to FIG. 10. In another example, a cohort identifier stored in association with the patient file may be accessed.

At step/operation 1106, a suggested medical code may be determined for the patient based on the patient vector; current symptom vector; and/or one or more trends, patterns, and/or the like identified based on patient vectors corresponding to a plurality of patients associated with the cohort identifier. For example, the visualization computing entity 200 may determine a suggested medical code based on the patient vector; current symptom vector; and/or one or more trends, patterns, and/or the like identified based on patient vectors corresponding to a plurality of patients associated with the cohort identifier. For example, patient vectors corresponding to a plurality of patients associated with the cohort identifier may be accessed and analyzed to identify trends, patterns, and/or the like. For example, trends, patterns, and/or the like corresponding and/or similar to the patient history of the patient (as encoded by the patient vector) and/or corresponding to the current symptom vector may be identified based on the patient vectors corresponding to a plurality of patients associated with the cohort identifier. The suggested body coordinate and/or medical code is the determined and/or identified based on the identified trends, patterns, and/or the like.

At step/operation 1108, the visualization comprising a point and/or zone corresponding to a suggested body coordinate and/or a suggested medical code is generated. For example, the visualization computing entity 200 may generate the visualization. For example, the graphical representation of the human body may be generated. In an example embodiment, generating the graphical representation of the human body comprising scaling the body model based on one or more patient characteristics (e.g., male/female, height, weight, waist measurement, hip measurement, eye color, hair color, amputation, body type/shape category, and/or other patient characteristic). For example, the sets of body coordinates are generated based on the body model and/or correspond to locations on a body model. The body model may be scaled based on one or more patient characteristics and the sets of body coordinates may be transformed based on the scaling of the body model. For example, the sets of body coordinates may be determined based on a standardized body model and to generate the visualization, the sets of body coordinates and the body model may be transformed to provide an individualized visualization for a patient. For example, if the body model is scaled based on the patient's height, the y-coordinate of each set of body characteristics may be transformed based on the scaling of the body model based on the patient's height. In an example embodiment, generating the visualization comprises identifying, marking, changing the coloring, and/or the like of the points and/or zones of the graphical representation of the human body located at and/or corresponding to the sets of body coordinates identified for the extracted and/or filtered medical codes corresponding to the patient's medical history. For example, the body part corresponding to the location indicated by a set of body coordinates corresponding to an extracted and/or filtered medical code may be highlighted on the graphical representation of the human body (e.g., the body part may be shown and/or may be shown in a color coded manner, a marker may be positioned at the point and/or zone indicated by the set of body coordinates and/or the like). For example, the marked points and/or zones of the graphical representation of the human body comprise at least one point and/or zone that corresponds to the suggested set of body coordinates and/or suggested medical code. In various embodiments, generating the visualization may comprise adding one or more labels to the graphical representation of the human body. For example, a label may provide information/data corresponding to a marked point or zone. For example, a label may include the medical code that corresponds to the set of body coordinates that identified the marked point and/or zone, a text description of the medical code that corresponds to the set of body coordinates that identified the marked point and/or zone, the date that a diagnosis corresponding to the point and/or zone was made, healthcare provider notes corresponding to the diagnosis corresponding to the point and/or zone, and/or the like.

The visualization may then be provided for rendering and displaying. For example, the visualization computing entity 200 may provide (e.g., transmit) the visualization such that a use computing entity 30 receives the visualization such that the user computing entity 30 may render and display the visualization. In an example embodiment, the visualization may be compressed before the visualization is provided. In an example embodiment, the visualization is provided such that the user computing entity 30 that generated and provided the visualization request receives the visualization. In an example embodiment, the visualization may be encoded in a secure manner for transmission. The user computing entity may receive, processes, and display the visualization as described with respect to FIG. 8.

f. Providing a Visualization of a Current Medical State Based on a Combination of the Current Symptoms Vector and Patient Vector In various embodiments, a visualization of a current medical state of a patient may be provided. In various embodiments, a current medical state of a patient is represented by at least one suggested set of body coordinates. In an example embodiment, a current medical state of a patient may be further represented by one or more sets of body coordinates corresponding to medical codes extracted from the patient's medical record. FIG. 12 provides a flowchart illustrating example procedures, processes, and/or operations to provide a visualization of a current medical state comprising a point or zone corresponding to a suggested medical code determined based on a combination of sets of body coordinates of a current symptom vector and/or patient vector, in accordance with an example embodiment of the present invention.

In various embodiments, a visualization request for a visualization of a current medical state of a patient is received. For example, the visualization computing entity 200 may receive a visualization request. For example, a user computing entity 30 may generate and provide (e.g., transmit) a visualization request such that the visualization computing entity 200 receives the visualization request. In various embodiments, the visualization request comprises a patient identifier (e.g., a patient's name, birthdate, all or last four digits of a social security number, or other patient identifier). In various embodiments, the visualization request indicates that the desired visualization is that of a current medical state of the patient. In an example embodiment, the visualization request comprises one or more current symptoms. For example, the visualization request may comprise a description and/or medical codes corresponding to one or more symptoms currently being experienced by the patient. In an example embodiment, the visualization request may comprise filter information/data that indicates which portion(s) of the patient's medical history should be visualized. For example, the filter information/data may indicate that the visualization should only include points and/or zones corresponding to sets of body coordinates that correspond to the last five years, last ten years, and/or the like of the patient's medical history. In another example, the filter information/data may indicate that the visualization should only include points and/or zones corresponding to sets of body coordinates that correspond to a particular diagnosis and complications and/or related diagnoses. For example, if a patient has type two diabetes, the filter information/data may indicate that the visualization should only provide information/data corresponding to diagnoses related to type two diabetes (e.g., hypertension, type two diabetes related nerve problems, and/or the like).

At step/operation 1202, responsive to receiving and processing the visualization request, a patient vector and/or current symptom vector is generated for the patient. For example, the visualization computing entity 200 may generate a patient vector and/or current symptom vector for the patient. For example, medical codes may be extracted from the patient's medical history. For example, the visualization computing entity 200 may securely access the patient's medical history (e.g., from memory 210, 215 and/or a data store stored in another computer-readable memory) and extract medical codes from the patient's medical history. In an example embodiment, only medical codes that satisfy the filter information/data are extracted from the patient's medical history. In another example embodiment, all of the medical codes are extracted from the patient's medical history and then the extracted medical codes are filtered based on the filter information/data. A set of body coordinates is determined and/or identified (e.g., using the code chart 600) for each extracted and/or filtered medical code and the determined and/or identified set of body coordinates are used to form a patient vector for the patient. In an example embodiment, one or more body coordinates corresponding to the current symptoms are determined. For example, if the patient reports sinus headaches as a current symptom, a set of body coordinates corresponding to a headache and/or the sinuses may be identified and/or determined. A current symptoms vector is generated and/or formed by adding the sets of body coordinates determined and/or identified based on the current symptoms provided in the visualization request to a vector and/or array.

At step/operation 1204, one or more sets of body coordinates from the patient vector and/or the current symptoms vector are combined to generate a suggested set of body coordinates and/or suggested medical code. For example, the visualization computing entity 200 may perform one or more operations to combine at least two sets of body coordinates from the current symptoms vector and, optionally, one or more sets of body coordinates from the patient vector to generate and/or determine a suggested set of body coordinates and/or a suggested medical code.

At step/operation 1206, the visualization comprising a point and/or zone corresponding to a suggested body coordinate and/or a suggested medical code is generated. For example, the visualization computing entity 200 may generate the visualization. For example, the graphical representation of the human body may be generated. In an example embodiment, generating the graphical representation of the human body comprising scaling the body model based on one or more patient characteristics (e.g., male/female, height, weight, waist measurement, hip measurement, eye color, hair color, amputation, body type/shape category, and/or other patient characteristic). For example, the sets of body coordinates are generated based on the body model and/or correspond to locations on a body model. The body model may be scaled based on one or more patient characteristics and the sets of body coordinates may be transformed based on the scaling of the body model. For example, the sets of body coordinates may be determined based on a standardized body model and to generate the visualization, the sets of body coordinates and the body model may be transformed to provide an individualized visualization for a patient. For example, if the body model is scaled based on the patient's height, the y-coordinate of each set of body characteristics may be transformed based on the scaling of the body model based on the patient's height. In an example embodiment, generating the visualization comprises identifying, marking, changing the coloring, and/or the like of the points and/or zones of the graphical representation of the human body located at and/or corresponding to the sets of body coordinates identified for the extracted and/or filtered medical codes corresponding to the patient's medical history. For example, the body part corresponding to the location indicated by a set of body coordinates corresponding to an extracted and/or filtered medical code may be highlighted on the graphical representation of the human body (e.g., the body part may be shown and/or may be shown in a color coded manner, a marker may be positioned at the point and/or zone indicated by the set of body coordinates and/or the like). For example, the marked points and/or zones of the graphical representation of the human body comprise at least one point and/or zone that corresponds to the suggested set of body coordinates and/or suggested medical code. In various embodiments, generating the visualization may comprise adding one or more labels to the graphical representation of the human body. For example, a label may provide information/data corresponding to a marked point or zone. For example, a label may include the medical code that corresponds to the set of body coordinates that identified the marked point and/or zone, a text description of the medical code that corresponds to the set of body coordinates that identified the marked point and/or zone, the date that a diagnosis corresponding to the point and/or zone was made, healthcare provider notes corresponding to the diagnosis corresponding to the point and/or zone, and/or the like.

The visualization may then be provided for rendering and displaying. For example, the visualization computing entity 200 may provide (e.g., transmit) the visualization such that a use computing entity 30 receives the visualization such that the user computing entity 30 may render and display the visualization. In an example embodiment, the visualization may be compressed before the visualization is provided. In an example embodiment, the visualization is provided such that the user computing entity 30 that generated and provided the visualization request receives the visualization. In an example embodiment, the visualization may be encoded in a secure manner for transmission. The user computing entity may receive, processes, and display the visualization as described with respect to FIG. 8.

g. Providing a Visualization of a Predicted Future Medical State

In various embodiments, a visualization of a predicted future medical state of a patient may be provided. In various embodiments, a predicted future medical state of a patient is represented by at least one predicted set of body coordinates. In an example embodiment, a predicted future medical state of a patient may be further represented by one or more sets of body coordinates corresponding to medical codes extracted from the patient's medical record. In an example embodiment, a long short term model (LSTM) of a neural network is used to determine the predicted set of body coordinates. FIG. 13 provides a flowchart illustrating example procedures, processes, and/or operations to provide a visualization of a predicted future medical state comprising a point or zone corresponding to a predicted set of body coordinates and/or a predicted medical code.

Starting at step/operation 1302, a prediction model is trained. In various embodiments, the prediction model is an LSTM. In various embodiments, an LSTM comprises internal contextual state cells that act as long-term or short-term memory cells. In various embodiments, the output of the LSTM is modulated by the state of the long-term and short-term memory cells. In various embodiments, the visualization computing entity 200 trains the predication model. For example, the prediction model may be trained based on a plurality of patient vectors that encode the medical history of a plurality of patients in sets of body coordinates. In an example embodiment, the sets of body coordinates of each patient vector are each associated with a time frame (e.g., a date and time) such that an order of medical events may be determined and/or the time between medical events encoded in a patient vector may be determined. In various embodiments, the prediction model is trained to receive a patient vector and to output a predicted future set of body coordinates. In an example embodiment, the prediction model is trained to receive a patient vector as input and to output one or more predicted future sets of body coordinates and a corresponding time period. For example, the prediction model may output a predicted future set of body coordinates corresponding to a patient's gall bladder and the time period of 5 years indicating that the prediction model predicts that the patient will have a medical event corresponding to the patient's gall bladder within five years and/or approximately five years from now. In an example embodiment, the prediction model may be configured to receive a patient vector and a predetermined time vector as input and provide at least one predicted future set of body coordinates as output, wherein the prediction model predicts that the patient will experience a medical event corresponding to the at least one predicted future set of body coordinates within the predetermined time period.

At a later point in time, at step/operation 1304, in various embodiments, a visualization request for a visualization of a predicted future medical state of a patient is received. For example, the visualization computing entity 200 may receive a visualization request. For example, a user computing entity 30 may generate and provide (e.g., transmit) a visualization request such that the visualization computing entity 200 receives the visualization request. In various embodiments, the visualization request comprises a patient identifier (e.g., a patient's name, birthdate, all or last four digits of a social security number, or other patient identifier). In various embodiments, the visualization request indicates that the desired visualization is that of a predicted future medical state of the patient. In an example embodiment, the visualization request comprises one or more current symptoms. For example, the visualization request may comprise a description and/or medical codes corresponding to one or more symptoms currently being experienced by the patient. In an example embodiment, the visualization request may comprise filter information/data that indicates which portion(s) of the patient's medical history should be visualized. For example, the filter information/data may indicate that the visualization should only include points and/or zones corresponding to sets of body coordinates that correspond to the last five years, last ten years, and/or the like of the patient's medical history. In another example, the filter information/data may indicate that the visualization should only include points and/or zones corresponding to sets of body coordinates that correspond to a particular diagnosis and complications and/or related diagnoses. For example, if a patient has type two diabetes, the filter information/data may indicate that the visualization should only provide information/data corresponding to diagnoses related to type two diabetes (e.g., hypertension, type two diabetes related nerve problems, and/or the like).

Responsive to receiving and processing the visualization request, a patient vector is generated for the patient. For example, the visualization computing entity 200 may generate a patient vector for the patient. For example, medical codes may be extracted from the patient's medical history. For example, the visualization computing entity 200 may securely access the patient's medical history (e.g., from memory 210, 215 and/or a data store stored in another computer-readable memory) and extract medical codes from the patient's medical history. In an example embodiment, only medical codes that satisfy the filter information/data are extracted from the patient's medical history. In another example embodiment, all of the medical codes are extracted from the patient's medical history and then the extracted medical codes are filtered based on the filter information/data. A set of body coordinates is determined and/or identified (e.g., using the code chart 600) for each extracted and/or filtered medical code and the determined and/or identified set of body coordinates are used to form a patient vector for the patient. The patient vector may then be provided as input to the trained prediction model. In an example embodiment, a predetermined time period and the patient vector are provided as input to the trained prediction model.

At step/operation 1306, one or more predicted future sets of body coordinates are received as output from the prediction model. In an example embodiment, a time period corresponding to each of the one or more predicted future sets of body coordinates is received. For example, the visualization computing entity 200 may receive one or more predicted future sets of body coordinates (and possibly corresponding time periods) are received as output of the prediction model. In an example embodiment, one or more predicted future medical codes may be determined and/or identified based on the predicted future set of body coordinates (e.g., using the code chart 600).

At step/operation 1308, the visualization comprising a point and/or zone corresponding to a predicted future body coordinate and/or a predicted future medical code is generated. For example, the visualization computing entity 200 may generate the visualization. For example, the graphical representation of the human body may be generated. In an example embodiment, generating the graphical representation of the human body comprising scaling the body model based on one or more patient characteristics (e.g., male/female, height, weight, waist measurement, hip measurement, eye color, hair color, amputation, body type/shape category, and/or other patient characteristic). For example, the sets of body coordinates are generated based on the body model and/or correspond to locations on a body model. To generate the graphical representation of the human body, the body model may be scaled based on one or more patient characteristics and the sets of body coordinates may be transformed based on the scaling of the body model. For example, the sets of body coordinates may be determined based on a standardized body model and to generate the visualization, the sets of body coordinates and the body model may be transformed to provide an individualized visualization for a patient. For example, if the body model is scaled based on the patient's height, the y-coordinate of each set of body characteristics may be transformed based on the scaling of the body model based on the patient's height. In an example embodiment, generating the visualization comprises identifying, marking, changing the coloring, and/or the like of the points and/or zones of the graphical representation of the human body located at and/or corresponding to the sets of body coordinates identified for the extracted and/or filtered medical codes corresponding to the patient's medical history. For example, the body part corresponding to the location indicated by a set of body coordinates corresponding to an extracted and/or filtered medical code may be highlighted on the graphical representation of the human body (e.g., the body part may be shown and/or may be shown in a color coded manner, a marker may be positioned at the point and/or zone indicated by the set of body coordinates and/or the like). For example, the marked points and/or zones of the graphical representation of the human body comprise at least one point and/or zone that corresponds to the predicted future set of body coordinates and/or predicted future medical code. In various embodiments, generating the visualization may comprise adding one or more labels to the graphical representation of the human body. For example, a label may provide information/data corresponding to a marked point or zone. For example, a label may include the medical code that corresponds to the set of body coordinates that identified the marked point and/or zone, a text description of the medical code that corresponds to the set of body coordinates that identified the marked point and/or zone, the date that a diagnosis corresponding to the point and/or zone was made, healthcare provider notes corresponding to the diagnosis corresponding to the point and/or zone, and/or the like.

The visualization may then be provided for rendering and displaying. For example, the visualization computing entity 200 may provide (e.g., transmit) the visualization such that a use computing entity 30 receives the visualization such that the user computing entity 30 may render and display the visualization. In an example embodiment, the visualization may be compressed before the visualization is provided. In an example embodiment, the visualization is provided such that the user computing entity 30 that generated and provided the visualization request receives the visualization. In an example embodiment, the visualization may be encoded in a secure manner for transmission. The user computing entity may receive, processes, and display the visualization as described with respect to FIG. 8.

V. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:
1. A method for generating a three-dimensional visualization of a predicted patient condition, the method comprising:
receiving, by a computing entity, a visualization request, wherein the visualization request comprises a patient indication and a predicted visualization type indication;
responsive to receiving the visualization request, generating, by the computing entity, an input vector for input into one or more machine learning models, wherein (a) the input vector represents a plurality of three-dimensional coordinates of a three-dimensional graphical representation of a human body, (b) each of the plurality of three-dimensional coordinates corresponds to a past medical condition, and (c) each of the plurality of three-dimensional coordinates is determined based at least in part on one or more alphanumeric medical codes;

generating, by the computing entity and using the one or more machine learning models and the input vector, a predicted three-dimensional coordinate, wherein the predicted three-dimensional coordinate corresponds to a predicted patient condition;

generating, by the computing entity, a three-dimensional graphical representation of a human body, wherein the three-dimensional graphical representation of the human body comprises (a) an indication of the predicted three-dimensional coordinate on the three-dimensional graphical representation of the human body, and (b) indication of the predicted medical condition; and providing, by the computing entity, the three-dimensional graphical representation of the human body for display by a user interface for an end user.

2. The method of claim 1, wherein the three-dimensional graphical representation of the human body is scaled based on one or more characteristics corresponding to the patient.

3. The method of claim 1, wherein the three-dimensional graphical representation provides a spatial representation of a past or present medical state of the patient.

4. The method of claim 1, wherein the three-dimensional graphical representation provides a spatial representation of a current medical state of the patient and the three-dimensional graphical representation comprises at least one suggested point and/or zone determined based at least in part on at least one of (a) one or more sets of body coordinates corresponding to medical codes of a health profile encoding the patient's medical history or (b) one or more sets of body coordinates corresponding to current symptoms of the patient.

5. The method of claim 1, wherein the three-dimensional graphical representation provides a spatial representation of a predicted future medical state of the patient and the visualization comprises at least one predicted point and/or zone determined based at least in part on one or more sets of body coordinates corresponding to medical codes of a health profile encoding the patient's medical history and a predictive model.

6. The method of claim 1, wherein the patient is associated with a cohort identified based at least in part on one or more sets of body coordinates corresponding to medical codes of a health profile encoding the patient's medical history and the method further comprises receiving and causing display of information corresponding to the cohort.

7. The method of claim 1, wherein the set of body coordinates corresponding to the medical code are determined by:

extracting one or more body part names from a code description corresponding to the medical code, the one or more body part names each identifying a body part corresponding to the medical code; and identifying the body coordinate corresponding to the body part based on a body model.

8. The method of claim 7, wherein the body model is generated by:

analyzing one or more anatomy maps by, for each anatomy map of the one or more anatomy maps:
identifying text printed on the anatomy map;
filtering text printed on the anatomy map to identify body part text;
matching instances of body part text to body part names identified based on medical code descriptions;
for each instance of body part text matched to a body part name identified based on the medical code descriptions, assigning coordinates to a body part shown on the anatomy map and corresponding to the instance of body part text; and
associating the coordinates with the body part name; and for each body part name having two or more sets of coordinates associated therewith, combining the two or more sets of coordinates to determine a set of body coordinates (a) associated with the body part name and (b) indicating a location of the body part identified by the body part name.

9. An apparatus comprising at least one processor and at least one memory including computer program code for one or more programs, the at least one processor in communication with a display device and at least one input device, the at least one memory and the computer program code configured to, with the at least one processor, cause the apparatus to perform at least the following:

receive a visualization request, wherein the visualization request comprises a patient indication and a predicted visualization type indication;

responsive to receiving the visualization request, generate an input vector for input into one or more machine learning models, wherein (a) the input vector represents a plurality of three-dimensional coordinates of a three-dimensional graphical representation of a human body, (b) each of the plurality of three-dimensional coordinates corresponds to a past medical condition, and (c) each of the plurality of three-dimensional coordinates is determined based at least in part on one or more alphanumeric medical codes;

generate, using the one or more machine learning models and the input vector, a predicted three-dimensional coordinate, wherein the predicted three-dimensional coordinate corresponds to a predicted patient condition;

generate a three-dimensional graphical representation of a human body, wherein the three-dimensional graphical representation of the human body comprises (a) an indication of the predicted three-dimensional coordinate on the three-dimensional graphical representation of the human body, and (b) indication of the predicted medical condition; and provide the three-dimensional graphical representation of the human body for display by a user interface for an end user.

10. The apparatus of claim 9, wherein the three-dimensional graphical representation of the human body is scaled based on one or more characteristics corresponding to the patient.

11. The apparatus of claim 9, wherein the three-dimensional graphical representation provides a spatial representation of a past or current medical state of the patient.

12. The apparatus of claim 9, wherein the three-dimensional graphical representation provides a spatial representation of a current medical state of the patient and the three-dimensional graphical representation comprises at least one suggested point and/or zone determined based at least in part on at least one of (a) one or more sets of body coordinates corresponding to medical codes of a health profile encoding the patient's medical history or (b) one or more sets of body coordinates corresponding to current symptoms of the patient.

13. The apparatus of claim 9, wherein the three-dimensional graphical representation provides a spatial representation of a predicted future medical state of the patient and the visualization comprises at least one predicted point and/or zone determined based at least in part on one or more sets of body coordinates corresponding to medical codes of a health profile encoding the patient's medical history and a predictive model.

14. The apparatus of claim 9, wherein the set of body coordinates corresponding to the medical code are determined by:
   extracting one or more body part names from a code description corresponding to the medical code, the one or more body part names each identifying a body part corresponding to the medical code; and
   identifying the body coordinate corresponding to the body part based on a body model.

15. The apparatus of claim 14, wherein the body model is generated by:
   analyzing one or more anatomy maps by, for each anatomy map of the one or more anatomy maps:
      identifying text printed on the anatomy map;
      filtering text printed on the anatomy map to identify body part text;
      matching instances of body part text to body part names identified based on medical code descriptions;
      for each instance of body part text matched to a body part name identified based on the medical code descriptions, assigning coordinates to a body part shown on the anatomy map and corresponding to the instance of body part text; and
      associating the coordinates with the body part name; and
   for each body part name having two or more sets of coordinates associated therewith, combining the two or more sets of coordinates to determine a set of body coordinates (a) associated with the body part name and (b) indicating a location of the body part identified by the body part name.

16. A computer program product comprising at least one non-transitory computer-readable storage medium having computer-executable program code portions stored therein, the computer-executable program code portions comprising program code instructions, the computer program code instructions, when executed by a processor of a computing entity, are configured to cause the computing entity to at least:
   receive a visualization request, wherein the visualization request comprises a patient indication and a visualization type indication;
   responsive to receiving the visualization request, generate an input vector for input into one or more machine learning models, wherein (a) the input vector represents a plurality of three-dimensional coordinates of a three-dimensional graphical representation of a human body, (b) each of the plurality of three-dimensional coordinates corresponds to a past medical condition, and (c) each of the plurality of three-dimensional coordinates is determined based at least in part on one or more alphanumeric medical codes;
   generate, by using the one or more machine learning models and the input vector, a predicted three-dimensional coordinate, wherein the predicted three-dimensional coordinate corresponds to a predicted patient condition;
   generate a three-dimensional graphical representation of a human body, wherein the three-dimensional graphical representation of the human body comprises (a) an indication of the predicted three-dimensional coordinate on the three-dimensional graphical representation of the human body, and (b) indication of the predicted medical condition; and
   provide the three-dimensional graphical representation of the human body for display by a user interface for an end user.

* * * * *

UNITED STATES PATENT AND TRADEMARK OFFICE
CERTIFICATE OF CORRECTION

PATENT NO. : 10,861,590 B2
APPLICATION NO. : 16/246789
DATED : December 8, 2020
INVENTOR(S) : White et al.

Page 1 of 1

It is certified that error appears in the above-identified patent and that said Letters Patent is hereby corrected as shown below:

On the Title Page

"Related U.S. Application Data
(63) Continuation of application No. 62/700,602, filed on July 19, 2019"
Should read:
--Related U.S. Application Data
(60) Provisional application No. 62/700,602, filed on July 19, 2019--

Signed and Sealed this
Nineteenth Day of January, 2021

Andrei Iancu
*Director of the United States Patent and Trademark Office*